(12) United States Patent
Chen et al.

(10) Patent No.: US 9,062,093 B2
(45) Date of Patent: Jun. 23, 2015

(54) PEPTIDE COMPOSITIONS AND METHODS FOR TREATING PATIENTS

(71) Applicant: THE REGENTS OF THE UNIVERSITY OF MICHIGAN, Ann Arbor, MI (US)

(72) Inventors: Yuqing E. Chen, Ann Arbor, MI (US); Changyong Xue, Ann Arbor, MI (US); Jifeng Zhang, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/087,247

(22) Filed: Nov. 22, 2013

(65) Prior Publication Data

US 2014/0148382 A1 May 29, 2014

Related U.S. Application Data

(62) Division of application No. 13/371,042, filed on Feb. 10, 2012, now Pat. No. 8,664,177.

(60) Provisional application No. 61/441,748, filed on Feb. 11, 2011.

(51) Int. Cl.
*A61K 38/06* (2006.01)
*C07K 5/04* (2006.01)
*C07K 5/08* (2006.01)
*C07K 5/083* (2006.01)

(52) U.S. Cl.
CPC ............... *C07K 5/0806* (2013.01); *A61K 38/06* (2013.01)

(58) Field of Classification Search
CPC ....... A61K 38/06; A61K 38/04; A61K 38/00; C07K 5/0808; C07K 5/0806; C07K 5/0804; C07K 5/0802; C07K 5/08; C07K 5/04; C07K 5/00
See application file for complete search history.

(56) References Cited

U.S. PATENT DOCUMENTS

| | | | |
|---|---|---|---|
| 3,215,685 A | 11/1965 | Kazuo et al. | |
| 3,795,664 A | 3/1974 | Tregear et al. | |
| 7,012,129 B2 | 3/2006 | Vahlne et al. | |
| 8,664,177 B2 | 3/2014 | Chen et al. | |
| 2005/0186146 A1 | 8/2005 | Gong et al. | |
| 2009/0221505 A1* | 9/2009 | Kolonin et al. | 514/13 |

FOREIGN PATENT DOCUMENTS

| | | |
|---|---|---|
| EP | 0187547 A2 | 7/1986 |
| EP | 2047848 A1 | 4/2009 |
| WO | WO-98/13384 A1 | 4/1998 |
| WO | WO-99/45941 A1 | 9/1999 |
| WO | WO-00/68695 A2 | 11/2000 |
| WO | WO-01/91700 A2 | 12/2001 |
| WO | WO-02/20722 A2 | 3/2002 |
| WO | WO-02/20723 A2 | 3/2002 |
| WO | WO-02/20769 A1 | 3/2002 |
| WO | WO-02/22211 A2 | 3/2002 |
| WO | WO-03/022991 A2 | 3/2003 |
| WO | WO-03/024995 A1 | 3/2003 |
| WO | WO-03/035028 A1 | 5/2003 |
| WO | WO-2004/016647 A2 | 2/2004 |
| WO | WO-2005/115457 A2 | 12/2005 |
| WO | WO-2006/108211 A1 | 10/2006 |
| WO | WO-2006/129095 A2 | 12/2006 |
| WO | WO-2007/015069 A2 | 2/2007 |
| WO | WO-2007/046818 A2 | 4/2007 |
| WO | WO-2008/021234 A2 | 2/2008 |
| WO | WO-2008/034391 A1 | 3/2008 |
| WO | WO-2011/010769 A1 | 1/2011 |

OTHER PUBLICATIONS

Carter et al., The Journal of Biological Chemistry (1998) vol. 273, No. 43, pp. 28277-28285.*
Barnett et al., Diabetes, Obesity and Metabolism. accepted article published online (2011).
Berge et al., Pharmaceutical Salts, *J. Pharmaceutical Sciences*, 66: 1-19 (1977).
Bergstrom et al., Amidation and Structure Relaxation Abolish the Neurotoxicity of the Prion Peptide PrP106-126 in Vivo and in Vitro, *J. Biol. Chem.*, 280: 23114-23121 (2005).
Chen et al., Evidence that the Diabetes Gene Encodes the Leptin Receptor: Identification of a Mutation in the Leptin Receptor Gene in db/db Mice, *Cell*, (3):491-495 (1996).
Clothe et al., Identification of a novel sodium-couple oligopeptide transporter (SOPT2) in mouse and human retinal pigment epithelial cells, Investigative & Visual Science, 51(1):413-20 (2010).
Dezaki et al., Blockade of Pancreatic Islet-Derived Ghrelin Enhances Insulin Secretion to Prevent High-Fat Diet-Induced Glucose Intolerance, *Diabetes*, 55 (12):3486-93 (2006).
Gannon and Nuttall, Amino Acid Ingestion and Glucose Metabolism—A review, *IUBMB Life*, 62: 660-668 (2010).
Gannon et al., The Insulin and Glucose Responses to Meals of Glucose Plus Various Proteins in Type II Diabetic Subjects, *Metabolism*, 37: 1081-1088 (1988).
Gannon et al., The metabolic response to ingested glycine1-3, *Am. J. Clin. Nutr.*, 76: 1302-1307 (2002).
Grieve et al., Emerging cardiovascular actions of the incretin hormone glucagon-like peptide-1: potential therapeutic benefits beyond glycaemic control?, *British J. Pharm.*, 157a: 1340-1351 (2009).
Hach et al., C-Peptide and its C-terminal fragments improve erythrocyte deformability in type 1 diabetes patients, *Exp. Diabetes Res.*, 1-6 (2008).
Hummel et al., Diabetes, a new mutation in the mouse, *Science*, 153 (740):1127-1128 (1966).
Hyaluron—Lifting-System-Antiwrinkle, downloaded from the Internet at <http://www..eng.hyaluron.ru/antiwrinkle/ on Sep. 27, 2013.

(Continued)

*Primary Examiner* — Karlheinz R Skowronek
*Assistant Examiner* — Catherine Mader
(74) *Attorney, Agent, or Firm* — Marshall, Gerstein & Borun LLP

(57) ABSTRACT

The present invention is directed to peptide compositions and methods of using the peptide compositions to treat prediabetes, diabetes, obesity, high blood pressure and metabolic syndrome.

20 Claims, 27 Drawing Sheets

(56) References Cited

OTHER PUBLICATIONS

Ido et al., Prevention of vascular and neural dysfunction in diabetic rats by C-peptide, *Science*, 277: 563-566 (1997).

International Search Report dated Nov. 7, 2012 for PCT/US2012/024684 filed Oct. 2, 2012.

John et al., N-terminal acetylation protects glucagon-like peptide GLP-1-(7-34)-amide from DPP-IV-mediated degradation retaining cAMP- and insulin-releasing capacity, *Eur. J. Med. Res.*, 13: 73-78 (2008).

Kalogeropoulou et al., Leucine, when ingested with glucose, synergistically stimulates insulin secretion and lowers blood glucose, *Metabolism*, 57: 1747-1752 (2008).

Liu et al., The exenatide analogue AC3174 attenuates hypertension, insulin resistance, and renal dysfunction in Dahl salt-sensitive rats, *Cardiovascular Diabetology*, 9(32): 1-10 (2010).

Ohtomo et al., Differential effects of proinsulin C-peptide fragments on Na+, K+—ATPase activity of renal tubule segments, *Diabetologia*, 41: 287-291 (1998).

Remington's Pharmaceutical Sciences, The Science and Practice of Pharmacy, 20th Edition, Lippincott Williams & White, Baltimore, Md. (2000).

Sato et al., C-peptide fragments stimulate flucose utilization in diabetic rats, *Cell. Mol. Life Sci.*, 61: 727-732 (2004).

Tomas et al., Glucagon-like peptide-1(9-36) amide metabolite inhibits weight gain and attenuates diabetes and hepatic steatosis in diet-induced obese mice, *Diabetes Obes. Metab.*, 13(1):26-33 (2011).

Yamauchi et al., The rat-derived hormone adiponectin reverses insulin resistance associated with both lipoatrophy and obesity, *Nat. Med.*, 7(8): 971-946 (2001).

Young et al., Glucose-lowering and insulin-sensitizing actions of exendin-4; Studies in obese diabetic (ob/ob, db/db) mice, diabetic fatty zucker rats, and diabetic rhesus monkeys (*Macaca mulatta*), *Diabetes*, 48:1026-1034 (1999).

\* cited by examiner

PEPTIDE COMPOSITIONS AND METHODS FOR TREATING PATIENTS

This application is a divisional of U.S. patent application Ser. No. 13/371,042 filed Feb. 10, 2012, which claims the benefit of the filing date of U.S. Provisional Patent Application No. 61/441,748 filed Feb. 11, 2011, which is incorporated by reference herein in its entirety.

STATEMENT OF GOVERNMENT INTEREST

This invention was made with government support under HL68878 and HL89544 awarded by the National Institutes of Health (NIH). The government has certain rights in the invention.

FIELD OF THE INVENTION

The present invention is directed to peptide compositions and methods of using the peptide compositions to treat prediabetes, diabetes, obesity, high blood pressure and metabolic syndrome.

BACKGROUND

Our bodies turn the food we eat into the sugar glucose. Blood transports glucose to cells which convert it into energy. Normally, a protein hormone called insulin controls the level of glucose in the blood. When there are defects in insulin production, insulin action, or both, high levels of glucose in the blood result. Diabetes is the group of diseases characterized by these defects.

The three most common forms of diabetes are type 1 diabetes, type 2 diabetes and gestational diabetes. Type 1 diabetes (previously known as insulin-dependent diabetes mellitus or juvenile-onset diabetes) usually develops in childhood or adolescence. It occurs when the body's immune system destroys the cells of the pancreas that produce insulin. People with type 1 diabetes must monitor the level of sugar in their blood multiple times a day and take insulin (via injections or a pump) to maintain an appropriate level. Gestational diabetes occurs when pregnant women become intolerant to glucose. Gestational diabetes also requires treatment to maintain appropriate glucose blood levels and avoid complications in the infant. Woman who have gestational diabetes are at increased risk for developing type 2 diabetes.

Type 2 diabetes (previously known as non-insulin-dependent diabetes mellitus or adult-onset diabetes) usually develops in adulthood. It develops as cells first do not use insulin properly and then the pancreas loses its ability to produce insulin. Many people with type 2 diabetes control their blood glucose with a meal plan, exercise program, losing weight and taking oral medication. Some people with type 2 diabetes need take insulin as well.

Diabetes is serious because too much sugar in the blood can damage the eyes, kidneys, nerves and heart. Complications of diabetes include heart disease, stroke, hypertension, blindness, other eye problems (such as diabetic retinopathy), kidney disease, nervous system disease (such as impaired sensation or pain in the feet or hands, slowed digestion of food, carpal tunnel syndrome and erectile dysfunction), amputations, periodontal disease, susceptibility to other illnesses (such as pneumonia and influenza), impaired mobility and depression. Uncontrolled diabetes can result in acute life-threatening events such as diabetic ketoacidosis and hyperosmolar coma.

Diabetes is the leading cause of kidney failure, non-traumatic lower limb amputations and new cases of blindness among adults in the United States. Diabetes is a major cause of heart disease and stroke. Diabetes was the seventh leading cause of death in the United States in 2007. Overall, the risk for death among people with diabetes is about twice that of people of similar age without diabetes. According to the Centers for Disease Control and Prevention, as of January 2011, diabetes affects 25.8 million people, 8.3% of the United States population. Another 79 million American adults are estimated to have prediabetes, a condition in which blood sugar levels are higher than normal but not high enough to be diagnosed as diabetes. Prediabetes is sometimes called impaired fasting glucose or impaired glucose tolerance. Prediabetes itself raises people's risk of type 2 diabetes, heart disease and stroke. Many prediabetics develop type 2 diabetes within ten years.

In addition to lifestyle interventions, prediabetic and type 2 diabetic patients are often treated with medications to address complications of diabetes. Doctors prescribe medications to control blood pressure and blood lipids to reduce cardiovascular complications. Often, in younger and heavier patients with normal kidney function, doctors prescribe the oral drug metformin to more directly address the defects causing diabetes. Metformin suppresses hepatic glucose production, increases insulin sensitivity, enhances peripheral glucose uptake, increases fatty acid oxidation and decreases absorption of glucose from the gastrointestinal tract. Metformin, though, is contraindicated in people with any condition that could increase the risk of lactic acidosis, including kidney disorders, lung disease and liver disease.

Other more recently approved drugs do not appear to be more effective than metformin and each has its own set of contraindications. For example, rosiglitazone was one of the first insulin-sensitizers used as an anti-diabetic drug. It renders fat cells more sensitive to insulin. Annual sales of rosiglitazone peaked at approximately $2.5 billion in 2006. Because rosiglitazone can be associated with an increased risk of cardiovascular events, the European Medicines Agency recommended the drug be suspended from the European market. The U.S. Food and Drug Agency has allowed it to remain on the market but it became subject to significant restrictions as of Sep. 23, 2010.

A precursor to insulin called human proinsulin C-peptide, and fragments of C-peptide, have also been investigated for the treatment of diabetes. See, International Publication Nos. WO 98/13384, WO 2002/022211, WO 2004/016647, WO 2006/129095 and WO 2007/015069. See also, Ohtomo et al., *Diabetologia*, 41: 287-291 (1998); Sato et al., *Cell. Mol. Life. Sci.*, 61: 727-732 (2004); Hach et al., *Exp. Diabetes Res.*: 1-6 (2008) and Ido et al., *Science*, 277: 563-566 (1997).

Food proteins are composed of twenty different amino acids and scientists have studied the effect of individual amino acids when ingested with glucose. See, Gannon and Nuttall, *IUBMB Life*, 62: 660-668 (2010); Gannon et al., *Metabolism*, 37: 1081-1088 (1988); Gannon et al., *Am. J. Clin. Nutr.*, 76: 1302-1307 (2002) and Kalogeropoulou et al., *Metabolism*, 57: 1747-1752 (2008). The amino acids leucine and glycine have been reported to attenuate the serum glucose response and stimulate additional insulin secretion. This effect requires the ingestion of significant amounts of the amino acids though, with accompanying bad taste, unbalanced amino acid intake and concerns of impairing renal function.

Glucagon-like peptide-1 (GLP-1) is an incretin hormone. Incretin hormones are secreted by intestinal cells in response to nutrient ingestion. The primary physiological function of GLP-1 appears to be related to glycemic control. GLP-1 stimulates insulin release, inhibits glucagon secretion, reduces gastric emptying and augments satiety. In patients with type 2 diabetes the incretin effect is reduced, contributing to impaired glycemic control. Administration of GLP-1 to patients has been reported to restore blood glucose regulation via endogenous insulin secretion. GLP-1 administration has also been reported to reduce energy intake through its actions of delaying gastric emptying and increasing satiety, therefore it may induce weight loss. Two GLP-receptor agonists/analogues are currently approved for treatment of type 2 diabetes mellitus, exenatide (Byetta®), and liraglutide (Victoza®) and others are in clinical development. A once-weekly formulation of exenatide (Bydureon®) has also been approved. See, Barnett et al., *Diabetes, Obesity and Metabolism*. accepted article published online (2011).

In addition, studies have demonstrated that agonists of the GLP-1 receptor also effect cardiovascular related functions such as heart rate and blood pressure. See, Grieve et al., *British J. Pharm.*, 157a: 1340-1351 (2009). In a particular study, Dahl salt-sensitive (DSS) rats were fed a high salt diet and treated with an exenatide mimetic (AC3174) alone or in combination with an ACE inhibitor (captopril). AC3174 had anti-hypertensive, insulin-sensitizing, and renoprotective effects comparable to that of captopril. See, Liu et al., *Cardiovascular Diabetology*, 9(32): 1-10 (2010).

There thus exists a need in the art for new treatments for prediabetes, diabetes and their complications. There also exists in the art a need for new treatments for obesity, high blood pressure and metabolic syndrome.

SUMMARY

The present invention provides products and methods for treating prediabetes, diabetes, obesity, high blood pressure, metabolic syndrome, poor glycemic control, and reduced insulin secretion.

The invention provides a method for treating a condition comprising administering to a patient an effective amount of a composition comprising at least one peptide consisting of the amino acid sequence GGL, GLG, LGL, LLG, LGG or GLL, or a pharmaceutically acceptable salt of the peptide, wherein the condition is prediabetes, diabetes, obesity, high blood pressure, metabolic syndrome, poor glycemic control, or reduced insulin secretion. In addition, the invention provides a method for treating a condition comprising administering to a patient an effective amount of a composition comprising at least one peptide consisting of the amino acid sequence GGdL, GdLG, GdLL, GLdL, GdLdL, dLLG, LdLG, dLdLG, dLGG, dLGL, LGdL, or dLGdL, or a pharmaceutically acceptable salt of the peptide, wherein the condition is prediabetes, diabetes, obesity, high blood pressure, metabolic syndrome, poor glycemic control, or reduced insulin secretion.

Also provided is a method of preventing, reducing, or ameliorating a diabetes-associated complication in a diabetic patient comprising administering to the patient an effective amount of a composition comprising at least one peptide consisting of the amino acid sequence GGL, GLG, LGL, LLG, LGG or GLL, or a pharmaceutically acceptable salt of the peptide, wherein the diabetes-associated complication is a cardiovascular disease, chronic kidney disease, kidney failure, bladder problems, erectile dysfunction, gastroporesis, an eye disease, a diabetic neuropathy, foot or skin ulcers, or lower extremity amputation. In addition, the invention provides a method of preventing, reducing, or ameliorating a diabetes-associated complication in a diabetic patient comprising administering to the patient an effective amount of a composition comprising at least one peptide consisting of the amino acid sequence GGdL, GdLG, GdLL, GLdL, GdLdL, dLLG, LdLG, dLdLG, dLGG, dLGL, LGdL or dLGdL, or a pharmaceutically acceptable salt of the peptide, wherein the diabetes-associated complication is a cardiovascular disease, chronic kidney disease, kidney failure, bladder problems, erectile dysfunction, gastroporesis, an eye disease, a diabetic neuropathy, foot or skin ulcers, or lower extremity amputation.

In all of the foregoing methods, the peptides can be acetylated at the N-terminus, amidated at the C-terminus, or both. The composition can be administered by an oral, intraperitoneal, ocular, intradermal, intranasal, subcutaneous, intramuscular or intravenous route.

The pharmaceutical compositions provided by the invention include a composition comprising at least one peptide consisting of the amino acid sequence GGL, GLG, GLL, GGdL, GdLG, GdLL, GLdL, GdLdL, dLLG, LdLG, dLdLG, dLGG, dLGL, LGdL or dLGdL, or a pharmaceutically acceptable salt of the peptide, and a pharmaceutically acceptable excipient. They also include a composition wherein the pharmaceutical composition comprises at least one peptide consisting of the amino acid sequence GGL, GLG, or GLL, or a pharmaceutically acceptable salt of the peptide, and a pharmaceutically acceptable excipient. In the compositions, the peptides can be acetylated at the N-terminus, amidated at the C-terminus, or both.

The invention provides a kit for administering a pharmaceutical composition comprising at least one peptide consisting of the amino acid sequence GGL, GLG, GLL, GGdL, GdLG, GdLL, GLdL, GdLdL, dLLG, LdLG, dLdLG, dLGG, dLGL, LGdL or dLGdL, or a pharmaceutically acceptable salt of the peptide, and a pharmaceutically acceptable excipient, wherein the kit comprises the composition, instructions for administration of the composition and a device for administering the composition to the patient. Additionally, the invention provides a kit wherein the pharmaceutical composition comprises at least one peptide consisting of the amino acid sequence GGL, GLG, or GLL. In the kits, the peptides can be acetylated at the N-terminus, amidated at the C-terminus, or both.

Cardiovascular diseases (CVD) are the primary cause of mortality among diabetic patients, accounting for almost two out of three deaths. Thus, minimization of risk of CVD is a critical clinical goal in the management of prediabetic and diabetic patients. The present invention provides products and methods that improve glycemic control and concurrently decrease the risk of cardiovascular events and other diabetes-related complications.

DETAILED DESCRIPTION

Figure 1:
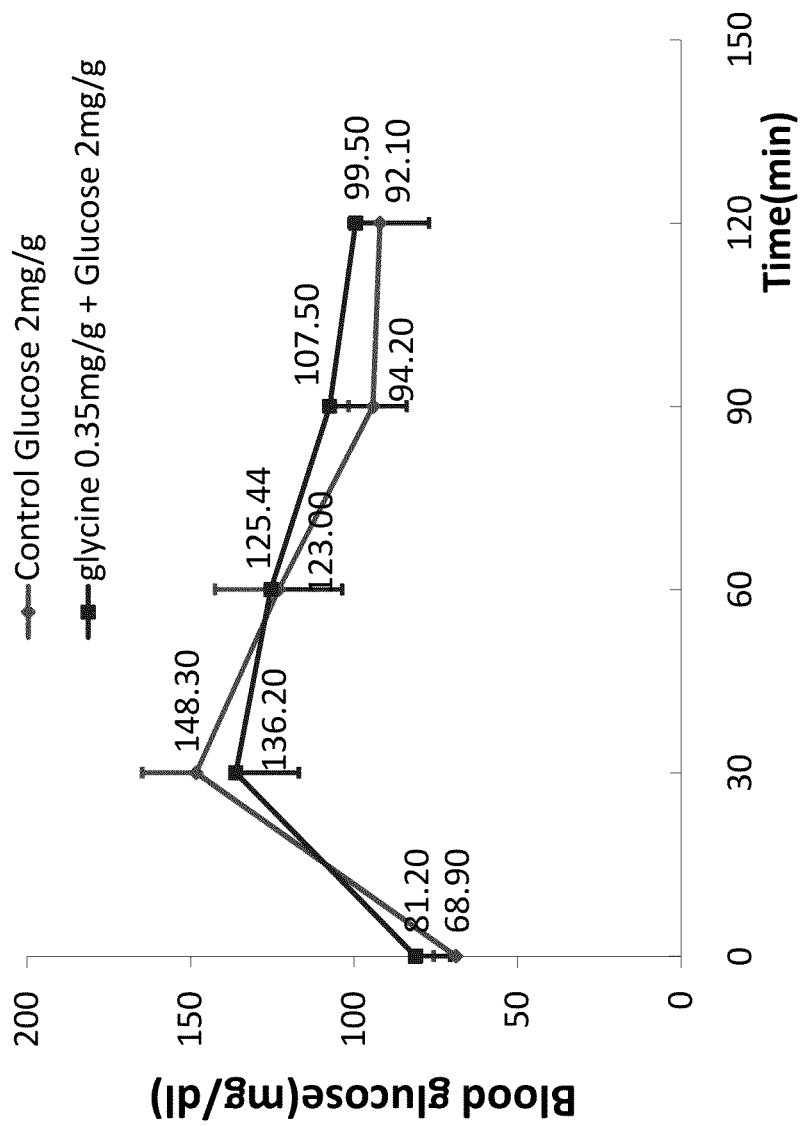
FIG. 1 shows the effect of glycine on blood glucose after oral load glycine and glucose in C57BL/6J mice.

In one aspect, the invention provides peptides to be administered to prediabetic or diabetic patients. Examples of peptides of the invention are GGL (termed "Diapin" herein), GLG, LGL, LLG, LGG and GLL. Other examples of peptides of the invention are GL and LG. The invention also provides for peptides GGL, GLG, LGL, LLG, LGG and GLL in which each leucine is independently in the form of the L-isomer or the D-isomer. Other examples of the peptides of the invention are LG and GL in which leucine is in the D-isomeric form. Peptides of the invention may be chemically synthesized or derived by digestion of proteins by methods known in the art.

As used herein, the singular forms "a", "an", and "the" include plural references unless the context clearly dictates otherwise.

It is known in the art that it is possible to substitute a chemically similar amino acid for an amino acid in a peptide or protein without negatively affecting the activity of the peptide or protein. Therefore, it is specifically contemplated that a glycine or leucine residue in a peptide of the invention may be substituted with a chemically similar amino acid residue such as a different aliphatic amino acid residue or an amino acid isomer. Other aliphatic amino acids are alanine, valine and isoleucine. It is also specifically contemplated that chemically similar amino acids may be added to one or both ends of a peptide of the invention without negatively affecting the activity of the peptide.

With the exception of glycine, the common amino acids all contain at least one chiral carbon atom. These amino acids therefore exist as pairs of stereoisomers designated as the L-isomer and the D-isomer. Most naturally occurring proteins and peptides are composed exclusively of the L-isomeric form. D-isomeric amino acids can affect the conformation of a peptide or protein and may lead to increased stability or a change in activity.

In some embodiments of the peptide, Leucine is replaced with D-Leucine. For example in some embodiments the peptide is Glycine-Glycine-Leucine (GGL), or is Glycine-Glycine-D-Leucine (GGdL), or is Glycine-Leucine-Glycine (GLG), or is Glycine-D-Leucine-Glycine (GdLG), or is Leucine-Leucine-Glycine (LLG), or is D-Leucine-Leucine-Glycine (dLLG), or is Leucine-D-Leucine-Glycine (LdLG), or is D-Leucine-D-Leucine-Glycine (dLdLG), or is Leucine-Leucine-Glycine (LLG), or is D-Leucine-Leucine-Glycine (dLLG), or is Leucine-D-Leucine-Glycine (LdLG), or is D-Leucine-D-Leucine-Glycine (dLdLG), or is Leucine-Glycine-Glycine (LGG), or is D-Leucine-Glycine-Glycine (dLGG), or is Glycine-Leucine-Leucine (GLL), or is Glycine-D-Leucine-Leucine (GdLL), or is Glycine-Leucine-D-Leucine (GLdL), or is Glycine-D-Leucine-D-Leucine (GdLdL), or is Leucine-Glycine (LG), or is D-Leucine-Glycine (dLG), or is Glycine-Leucine (GL), or is Glycine-D-Leucine (GdL). The peptides of the invention may be used individually or used as a mixture of two or more peptides. With respect to a mixture, each possible subcombination of peptides is specifically contemplated by the invention.

In some embodiments, peptides of the invention are chemically modified. In some embodiments peptides of the invention are acetylated at the N-terminus. In some embodiments, peptides of the invention are amidated at the C-terminus. In some embodiments, peptides of the invention are acetylated at the N-terminus and amidated at the C-terminus. Peptides are acetylated or amidated by methods known in the art. In some embodiments of the present disclosure, the peptide is glycosylated, carboxylated, phosphorylated, esterified, or converted into an acid addition salt and/or optionally dimerized, polymerized, pegylated, or otherwise conjugated.

In some embodiments, the peptides comprise one or more non-peptide bonds in place of peptide bond(s). For example, the peptides comprise in place of a peptide bond, an ester bond, an ether bond, a thioether bond or an amide bond.

In another aspect, compositions of at least one of the peptides of the invention are provided. Examples of compositions of the invention are compositions comprising one or more of the peptides GGL, GLG, LGL, LLG, LGG and GLL, or a pharmaceutically acceptable salt thereof. Other examples of compositions of the invention are compositions comprising one or more of the peptides GL and LG, or pharmaceutically acceptable salts thereof. Other examples of compositions of the invention are compositions comprising GGL, GLG, GLL, LLG, LGG, LGL, GGdL, GdLG, GdLL, GLdL, GdLdL, dLLG, LdLG, dLdLG, dLGG, dLGL, LGdL, dLGdL, or a pharmaceutically acceptable salt thereof. The compositions of the invention may include other components, including other amino acids. With respect to the compositions, each possible subcombination of peptides is specifically contemplated by the invention.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention. Pharmaceutically acceptable salts are well known in the art. For example, Berge et al. describe pharmaceutically acceptable salts in detail in *J. Pharmaceutical Sciences*, 66: 1-19 (1977).

It is contemplated the peptides of the invention, or mixtures thereof, can be used as the sole active product ingredient in the composition. Accordingly in an aspect of the invention, compositions of one or more of the peptides of the invention are provided wherein the peptide or peptides of the invention are the sole active ingredient. Thus, an embodiment of the present disclosure is a composition consisting essentially of at least one peptide consisting of the amino acid sequence GGL, GLG, LGL, LLG, LGG or GLL, or pharmaceutically acceptable salts thereof. Another embodiment is a composition consisting essentially of at least one peptide consisting of the amino acid sequence GL or LG, or pharmaceutically acceptable salts thereof. Yet another embodiment is a composition consisting essentially of at least one peptide consisting of the amino acid sequence GGL, GLG, GLL, LLG, LGG, LGL, GGdL, GdLG, GdLL, GLdL, GdLdL, dLLG, LdLG, dLdLG, dLGG, dLGL, LGdL, dLGdL, or a pharmaceutically acceptable salt thereof. With respect to the compositions, each possible subcombination of peptides is specifically contemplated by the invention.

In yet a further aspect, the invention provides a composition comprising at least one peptide of the invention and a pharmaceutically acceptable excipient.

In some embodiments, a pharmaceutical composition comprises at least one peptide consisting of the amino acid sequence GGL, GLG, GLL, GGdL, GdLG, GdLL, GLdL, GdLdL, dLLG, LdLG, dLdLG, dLGG, dLGL, LGdL or dLGdL, or a pharmaceutically acceptable salt of the peptide, and a pharmaceutically acceptable excipient. In some embodiments, the pharmaceutical composition comprises at least one peptide consisting of the amino acid sequence GGL, GLG, or GLL, or a pharmaceutically acceptable salt of the peptide, and a pharmaceutically acceptable excipient. In some embodiments, the pharmaceutical composition comprises the peptide consisting of the amino acid sequence GGL, or a pharmaceutically acceptable salt of the peptide, and a pharmaceutically acceptable excipient. With respect to the pharmaceutical compositions, each possible subcombination of peptides is specifically contemplated by the invention.

Pharmaceutical compositions of the invention are formulated with pharmaceutically acceptable excipients such as carriers, solvents, stabilizers, adjuvants, diluents, etc., depending upon the particular mode of administration and dosage form. The compositions are generally formulated to achieve a physiologically compatible pH, and range from a pH of about 3 to a pH of about 11, about pH 3 to about pH 7, depending on the formulation and route of administration. In alternative embodiments, the pH is adjusted to a range from about pH 5.0 to about pH 8. In various aspects, the compositions comprise a therapeutically effective amount of at least one peptide as described herein, together with one or more pharmaceutically acceptable excipients. The compositions may include a second active ingredient useful in the treatment or prevention of bacterial growth (for example and without limitation, anti-bacterial or anti-microbial agents).

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol) wetting or emulsifying agents, pH buffering substances, and the like.

Pharmaceutical compositions suitable for the delivery of peptides of the present invention and methods for their preparation will be readily apparent to those skilled in the art. Such compositions and methods for their preparation may be found, for example, in Remington's Pharmaceutical Sciences, The Science and Practice of Pharmacy, 20th Edition, Lippincott Williams & White, Baltimore, Md. (2000). The peptides of the present invention may be formulated to be immediate and/or modified release.

In yet another aspect, the invention provides a method for treating a condition comprising administering to a patient an effective amount of a composition comprising at least one peptide consisting of the amino acid sequence GGL, GLG, LGL, LLG, LGG or GLL, or a pharmaceutically acceptable salt of the peptide, wherein the condition is prediabetes, diabetes, obesity, high blood pressure, metabolic syndrome, poor glycemic control, or reduced insulin secretion. The invention also provides a method for treating a condition comprising administering to a patient an effective amount of a composition comprising at least one peptide consisting of the amino acid sequence GGdL, GdLG, GdLL, GLdL, GdLdL, dLLG, LdLG, dLdLG, dLGG, dLGL, LGdL, or dLGdL, or a pharmaceutically acceptable salt of the peptide, wherein the condition is prediabetes, diabetes, obesity, high blood pressure, metabolic syndrome, poor glycemic control, or reduced insulin secretion. With respect to the methods, each possible subcombination of peptides is specifically contemplated by the invention.

In some embodiments, the invention provides a method for treating a prediabetic or diabetic patient comprises administering to the patient a composition comprising at least one of the peptides GGL, GLG, LGL, LLG and GLL. In some embodiments, the invention also provides a method for treating a prediabetic or diabetic patient comprising administering to the patient a composition comprising at least one of peptide GL or LG. In some embodiments, the diabetes is type 1 diabetes. In some embodiments, the diabetes is type 2 diabetes. The amount of the composition administered is therapeutically effective to achieve at least one of the following: reducing blood glucose levels, stimulating insulin secretion, stimulating GLP-1 secretion, reducing insulin resistance, and improving glycemic control.

The term "treating" (or other forms of the word such as "treatment" or "treat") is used herein to mean that administration of a composition of the present invention mitigates a condition in a patient and/or reduces, inhibits, or eliminates a particular characteristic or event associated with a condition. Thus, the term "treatment" includes, preventing a condition from occurring in a patient, particularly when the patient is predisposed to acquiring the condition; reducing or inhibiting the condition; and/or ameliorating or reversing the condition. Insofar as the methods of the present invention are directed to preventing conditions, it is understood that the term "prevent" does not require that the condition be completely thwarted. Rather, as used herein, the term preventing refers to the ability of the skilled artisan to identify a population that is susceptible to condition, such that administration of the compositions of the present invention may occur prior to onset of the condition. The term does not imply that the condition must be completely avoided.

An "effective amount" as used herein refers to an amount of a peptide of the invention sufficient to exhibit a detectable therapeutic effect. The effect is detected by, for example, an improvement in clinical condition, or a prevention, reduction or amelioration of complications. The precise effective amount for a patient will depend upon the patient's body weight, size, and health; the nature and extent of the condition; and the therapeutic or combination of therapeutics selected for administration. Therapeutically effective amounts for a given situation are determined by routine experimentation that is within the skill and judgment of the clinician.

In some embodiments, the invention provides methods for treating obesity, high blood pressure or metabolic syndrome. Accordingly, one embodiment of the invention is a method for treating obesity comprising administering to a patient an effective amount of composition comprising at least one peptide consisting of the amino acid sequence GGL, GLG, LGL, LLG, LGG, GLL, LG, or GL, or a pharmaceutically acceptable salt thereof. Still another embodiment is a method for treating high blood pressure comprising administering to a patient an effective amount of a composition comprising at least one peptide consisting of the amino acid sequence GGL, GLG, LGL, LLG, LGG, GLL, LG, or GL, or a pharmaceutically acceptable salt thereof. Another embodiment is a method for treating metabolic syndrome comprising administering to a patient an effective amount of a composition comprising at least one peptide consisting of the amino acid sequence GGL, GLG, LGL, LLG, LGG, GLL, LG, or GL, or a pharmaceutically acceptable salt thereof. In any of the foregoing embodiments, one or more leucine in the peptide is independently replaced with the D-isomer of leucine. With respect to the methods, each possible subcombination of peptides is specifically contemplated by the invention.

In still another aspect, the invention provides methods for preventing, reducing and/or ameliorating diabetes-associated complications in a prediabetic or diabetic patient comprising administering to the patient a composition comprising at least one peptide consisting of the amino acid sequence GGL, GLG, LGL, LLG, LGG or GLL. The invention also provides methods for preventing, reducing and/or ameliorating diabetes-associated complications in a prediabetic or diabetic patient comprising administering to the patient a composition comprising at least one of the peptides consisting of the amino acid sequence GL or LG. It also provides a method of preventing, reducing, or ameliorating a diabetes-associated complication in a diabetic patient comprising administering to the patient an effective amount of a composition comprising at least one peptide consisting of the amino acid sequence GGL, GLG, LGL, LLG, LGG or GLL, or a pharmaceutically acceptable salt of the peptide. It also provides a method of preventing, reducing, or ameliorating a diabetes-associated complication in a diabetic patient comprising administering to the patient an effective amount of a composition comprising at least one peptide consisting of the amino acid sequence GGdL, GdLG, GdLL, GLdL, GdLdL, dLLG, LdLG, dLdLG, dLGG, dLGL, LGdL or dLGdL, or a pharmaceutically acceptable salt of the peptide. With respect to the methods, each possible subcombination of peptides is specifically contemplated by the invention. In some embodiments, the diabetes is type 1 diabetes. In some embodiments, the diabetes is type 2 diabetes. The administration is of an amount of the composition that is therapeutically effective to prevent, reduce or ameliorate at least one diabetes-associated complication including, but not limited to, the following: a cardiovascular disease [e.g., coronary artery disease (sometimes called ischemic heart disease), cerebral vascular diseases (such as stroke or transient ischemic attacks), heart failure, atherosclerosis, or peripheral arterial disease], chronic kidney disease, kidney failure, bladder problems, erectile dysfunction, gastroporesis, an eye disease (such as diabetic retinopathy, cataract or glaucoma), a diabetic neuropathy (peripheral, autonomic, proximal or focal), foot or skin ulcers, or lower extremity amputation.

The compounds of the present invention may be administered by any suitable route. For example, compositions of the invention can be administered by the oral, ocular, intradermal, intraperitoneal ("ip"), intranasal, subcutaneous, intramuscular or intravenous route.

Formulations suitable for oral administration include, for example, solid, semi-solid and liquid systems such as, tablets; soft or hard capsules containing multi- or nano-particulates, liquids, or powders; lozenges (including liquid-filled); chews; gels; fast dispersing dosage forms; films; ovules; sprays. In some embodiments the peptides of the present invention are formulated for oral administration using delivery vehicles known in the art, including but not limited to, microspheres, liposomes, enteric coated dry emulsions or nanoparticles.

Liquid dosage forms for oral administration include, but are not limited to, pharmaceutically acceptable emulsions, microemulsions, solutions, suspensions, syrups and elixirs. In addition to the active peptides, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active peptide is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. The active compounds can also be in microencapsulated form with one or more excipients as noted above. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Treatment of pre-diabetic or diabetic patients with compositions of the invention in combination with other diabetes drugs known in the art is specifically contemplated. In some embodiments, treatment with compositions of the invention allows a reduction in the dose of the other diabetes drug or drugs and therefore reduces the side effects associated with the other drug or drugs. In some embodiments, the other diabetes drug is insulin. In some embodiments, the other diabetes drug is a biguanide (such as metformin). In some embodiments, the other diabetes drug is a thiazolidinedione (such as pioglitazone). In some embodiments, the other diabetes drug is a DPP-4 inhibitor (such as sitagliptin). In other words, compositions of the present invention can be used in combination with other drugs such as those used as standard of care for the condition being treated. In some embodiments the drug is a statin (including but not limited to, atorvastatin, lovastatin, simvastatin, pravastatin rosuvastatin, fluvastatin, and pitastatin). In some embodiments, the drug is a blood pressure lowering drug [including but not limited to, Angiotensin-converting enzyme (ACE) inhibitors such as captopril, lisinopril, and ramipril; Angiotensin II receptor blockers such as losartan, olmesartan and valsartan; beta blockers such as metoprolol, nadolol and penbutolol; and calcium channel blockers such as amlodipine, diltiazem and nifedipine].

In still another aspect, the invention provides a kit for administering a composition of invention to a patient in need thereof, where the kit comprises a composition of invention, instructions for use of the composition and a device for administering the composition to the patient. In some embodiments, a kit for administering a pharmaceutical composition comprises at least one peptide consisting of the amino acid sequence GGL, GLG, GLL, LLG, LGL, LGG, GGdL, GdLG, GdLL, GLdL, GdLdL, dLLG, LdLG, dLdLG, dLGG, dLGL, LGdL or dLGdL, or a pharmaceutically acceptable salt of the peptide, and a pharmaceutically acceptable excipient, wherein the kit comprises the composition, instructions for administration of the composition and a device for administering the composition to the patient. In some embodiments, the kit comprises a pharmaceutical composition comprising at least one peptide consisting of the amino acid sequence GGL, GLG, or GLL. With respect to the kits, each possible subcombination of peptides is specifically contemplated by the invention.

EXAMPLES

The invention will be more fully understood by reference to the following examples which detail exemplary embodiments of the invention.

Example 1

The effects of the amino acids glycine and leucine on blood glucose were determined.
Effect of Glycine on Blood Glucose after Oral Load Glycine and Glucose An experiment was performed in adult male C57BL/6J mice purchased from Jackson Lab (Bar Harbor, Me.). Fasted mice were given glucose (2 mg/g body weight, diamond line in FIG. 1, n=10) or glycine (0.35 mg/g bw, square line in FIG. 1, n=10) and glucose by gavaging. Blood glucose was measured at 0, 30, 60, 90, and 120 min after giving glucose.

Figure 2:
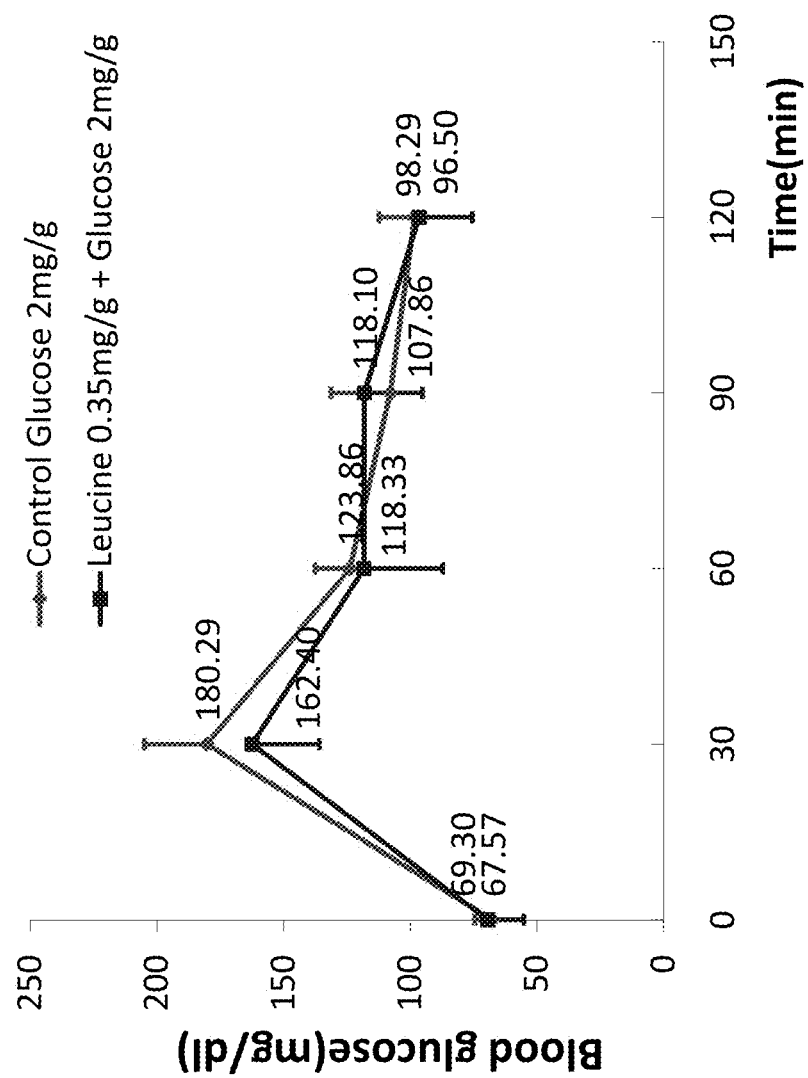
FIG. 2 shows the effect of leucine on blood glucose after oral load leucine and glucose in C57BL/6J mice.

Blood glucose levels at any time point in the glycine group were not significantly changed compared to the control group.
Effect of Leucine on Blood Glucose after Oral Load Leucine and Glucose An experiment was performed in adult male C57BL/6J mice purchased from Jackson Lab. Fasted mice were given glucose (2 mg/g body weight, diamond line in FIG. 2, n=10) or Leucine (0.35 mg/g bw, square line in FIG. 2, n=10) and glucose by gavaging. Blood glucose was measured at 0, 30, 60, 90, 120 min after giving glucose.

Example 2

Figure 3:
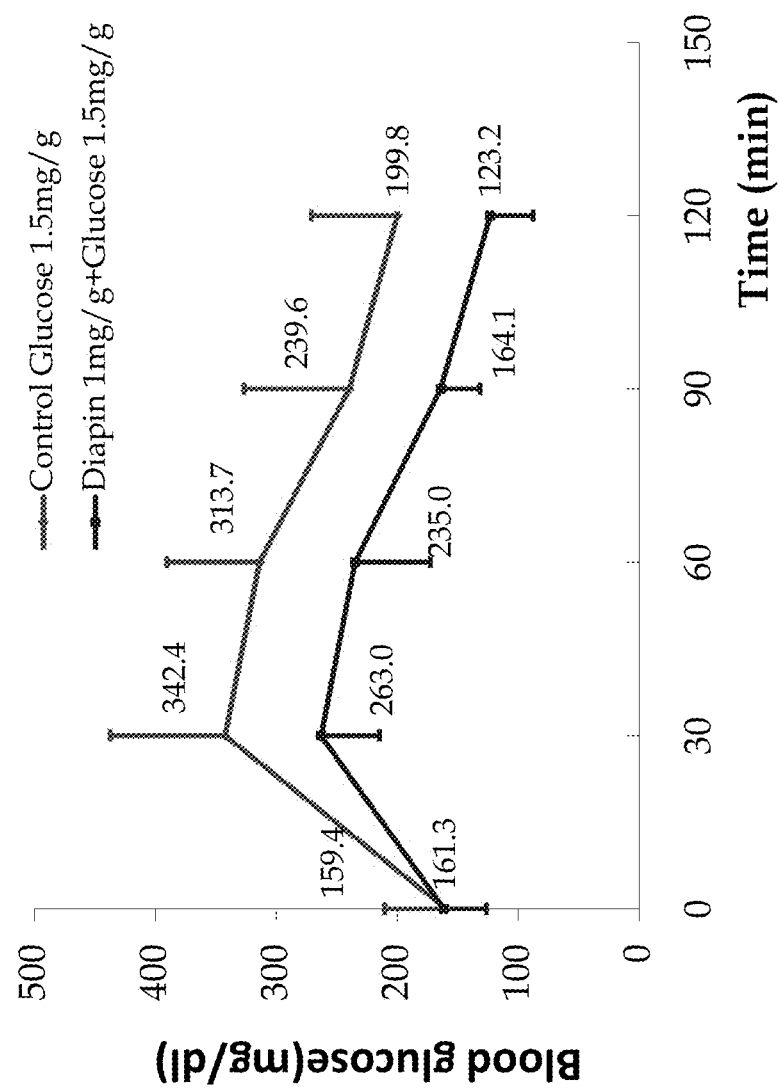
FIG. 3 shows Diapin inhibits the increase of blood glucose after oral load of glucose in KKay diabetic mice.
Figure 4:
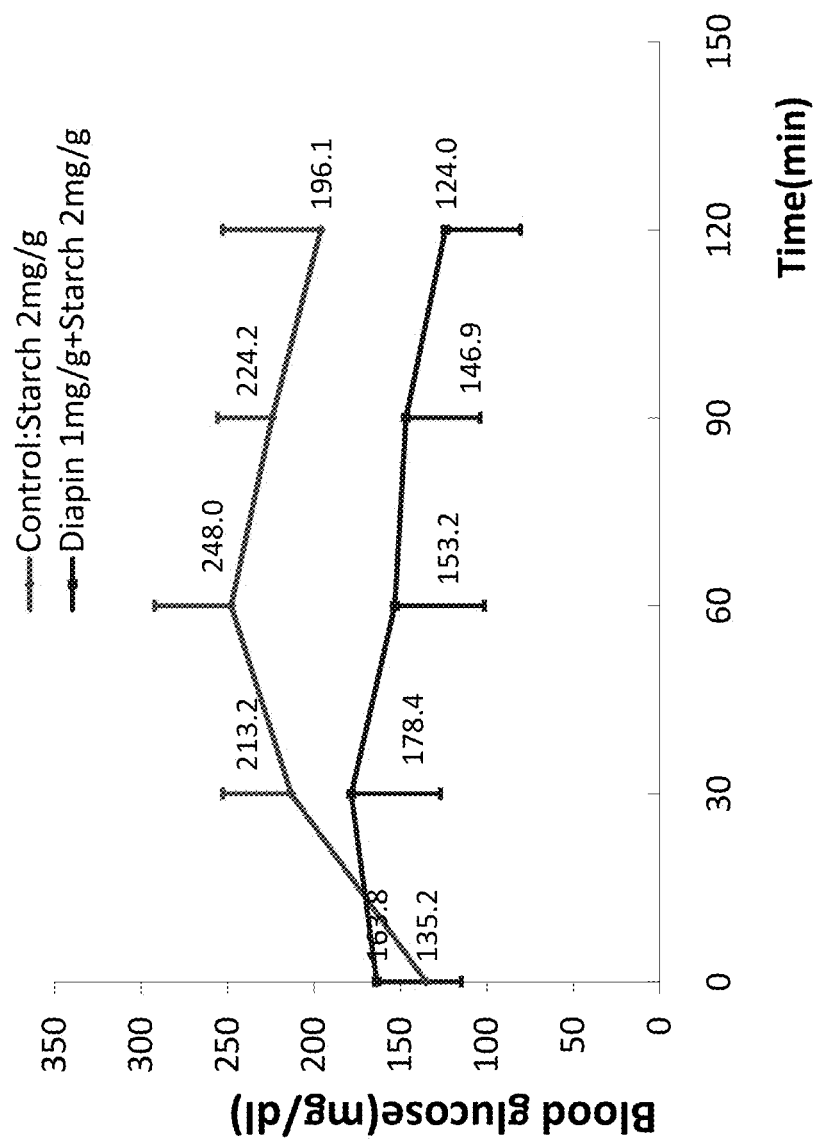
FIG. 4 show Diapin inhibits the increase of blood glucose after oral load of starch in KKay diabetic mice.

Diapin (peptide GGL of the invention) potently attenuates blood glucose levels when orally ingested with either glucose or starch in a diabetic mouse. Moreover, Diapin also reduces blood glucose levels under non-fasting condition in KKay diabetic mice [Yamauchi et al., *Nat. Med.*, 7(8): 971-946 (2001)]. See FIG. 3.
Diapin Inhibits the Increase of Blood Glucose after Oral Load of Glucose in Diabetic Mice Blood glucose levels at 30, 60, 90 and 120 min in Diapin group was significantly lower than those in the control.
Diapin Inhibits the Increase in Blood Glucose after Oral Load of Starch in Diabetic Mice An experiment was performed in adult male KKay diabetic mice purchased from the Jackson Lab. In the control group (diamond line in FIG. 4, n=10), starch was orally administered at dose of 2 mg/g bw. In the Diapin group (square line in FIG. 4, n=9), starch and Diapin were orally administered at dose of 2 mg/g bw and 1 mg/g bw, respectively. Blood glucose was measured at 0, 30, 60, 90 and 120 min after gavaging starch and Diapin.

Figure 5:
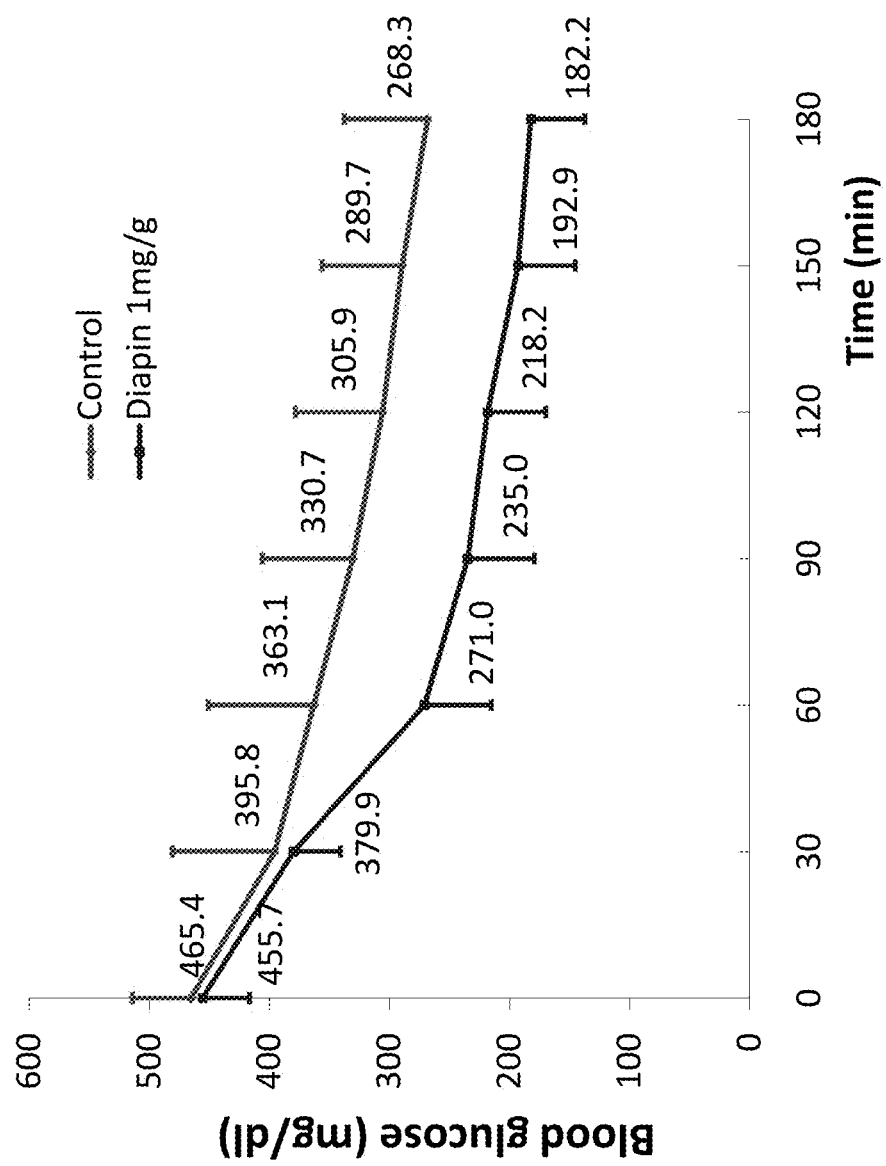
FIG. 5 shows Diapin reduces random blood glucose in KKay diabetic mice.

Blood glucose levels at 30, 60, 90 and 120 min in the Diapin group was significantly lower than those in the control.
Diapin Reduces Random Blood Glucose in Diabetic Mice An experiment was performed in adult male KKay diabetic mice purchased from the Jackson Lab. Under non-fasting condition, in the control group (diamond line in FIG. 5, n=9), distilled water was orally given and in the Diapin group (square line in FIG. 5, n=9), Diapin was orally administered at 1 mg/g bw. Blood glucose was measured at 0, 30, 60, 90, 120, 150 and 180 min after gavaging of Diapin.

Blood glucose levels at 60, 90, 120, 150 and 180 min in the Diapin group were significantly lower than those in the control.

Example 3

Figure 6:
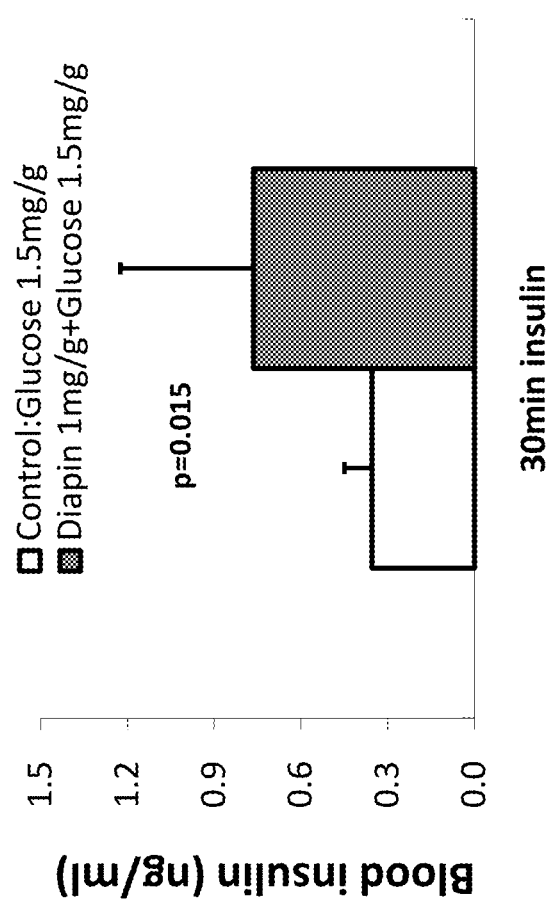
FIG. 6 shows Diapin stimulates insulin secretion in KKay diabetic mice 30 min after oral load of glucose and Diapin.

Diapin per se stimulates insulin secretion in KKay diabetic mice. Furthermore, Diapin also increases GLP-1 secretion in diabetic mice.
Diapin Stimulates Insulin Secretion in Diabetic Mice after Oral Load of Glucose and Diapin An experiment was performed in adult male KKay diabetic mice. Under fasting conditions in the control group (white bar in FIG. 6, n=11), glucose was orally administered at dose of 1.5 mg/g bw. In the Diapin group (black bar in FIG. 6, n=11), Diapin and glucose were orally administered at 1 mg/g bw and 1.5 mg/g bw, respectively. Blood samples were collected at 30 min after oral administration of glucose and Diapin. Blood glucose was monitored with FreeStyle glucose meter and insulin was measured by ELISA (Alpco, Cat#80-INSMS-E01).

Figure 7:
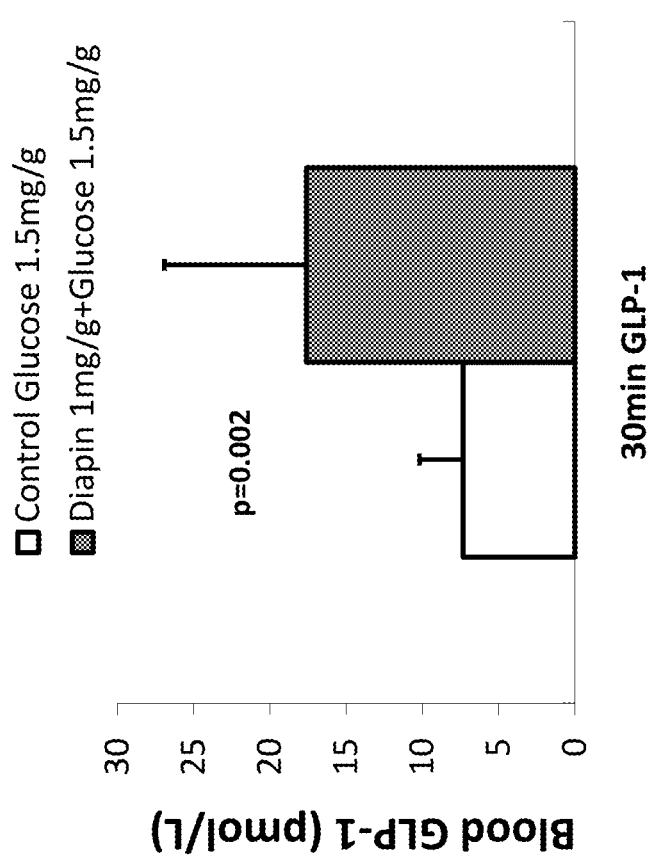
FIG. 7 shows Diapin stimulates GLP-1 secretion in KKay diabetic mice 30 min after oral load of glucose and Diapin.

Diapin stimulated insulin secretion in the KKay diabetic mice.
Diapin Stimulates GLP-1 Secretion in Diabetic Mice after Oral Load of Glucose and Diapin An experiment was performed in adult male KKay diabetic mice. Under fasting conditions, in the control group (white bar in FIG. 7, n=11), glucose was orally administered at dose of 1.5 mg/g bw and in the Diapin group (black bar in FIG. 7, n=11), Diapin and glucose were orally administered at 1 mg/g bw and 1.5 mg/g bw, respectively. Blood samples were collected at 30 min after oral administration of glucose and Diapin. GLP-1 was measured by ELISA (Alpco, Cat#43-GP1HU-E01).

Diapin also increases GLP-1 secretion in diabetic mice.

Example 4

Diapin ingested with diet decreases random blood glucose levels in KKay diabetic mice in a time- and dose-dependent manner.

Figure 8:
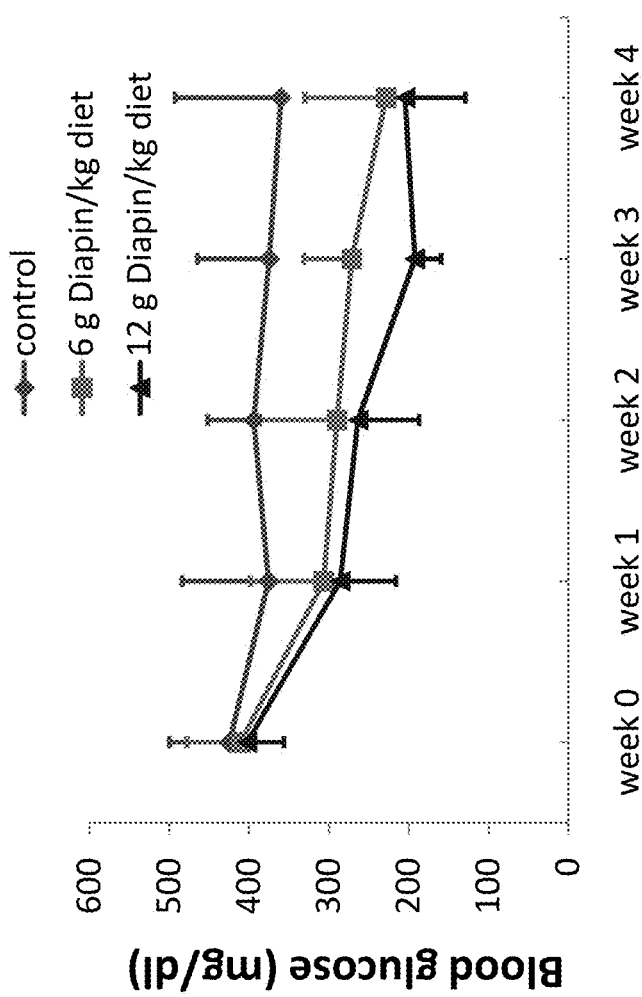
FIG. 8 shows Diapin decreases the blood glucose level of KKay diabetes mouse in a time- and dose-dependent manner.

An experiment was performed in adult male KKay diabetic mice. The mice were divided into three groups of 10 animals each and fed, ad libitum, regular chow (control), chow, chow mixed with 6 g Diapin/kg, or chow mixed with 12 g Diapin/kg for the duration of the experiment. Blood glucose levels were measured weekly in the early morning at initiation (week 0), and weekly thereafter for 4 weeks. Results are shown in FIG. 8.

Blood glucose levels in both groups fed with chow mixed with Diapin were significantly lower than those in the control.

Example 5

Figure 9:
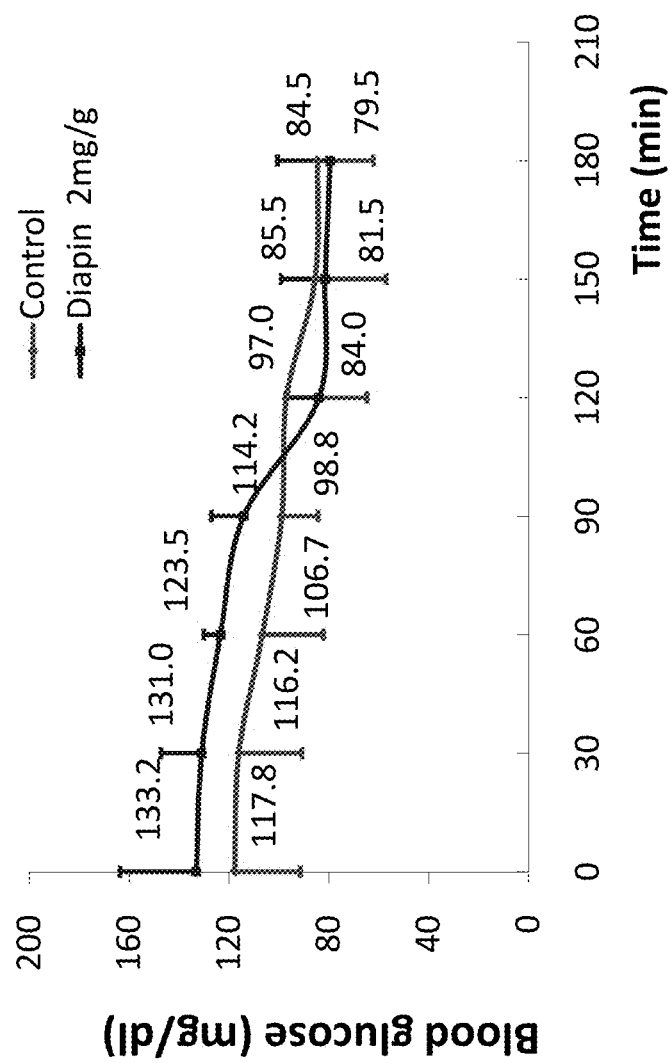
FIG. 9 shows Diapin has no effect on fasting blood glucose levels in C57BL/6J mice.

Diapin does not reduce blood glucose levels in non-diabetic C57BL/6J mice when blood glucose levels are at normal levels.
Diapin has No Effect on Fasting Blood Glucose Levels in C57BL/6J Mice An experiment was performed in adult male C57BL/6J mice purchased from Jackson Lab. The mice were given water (diamond line in FIG. 9, n=6) or Diapin (2 mg/g bw, square line in FIG. 9, n=6). Blood glucose was measured at 0, 30, 60, 90, 120, 150 and 180 min after oral administration of Diapin.

There was no significant difference in blood glucose levels between the groups.

Example 6

Figure 10:
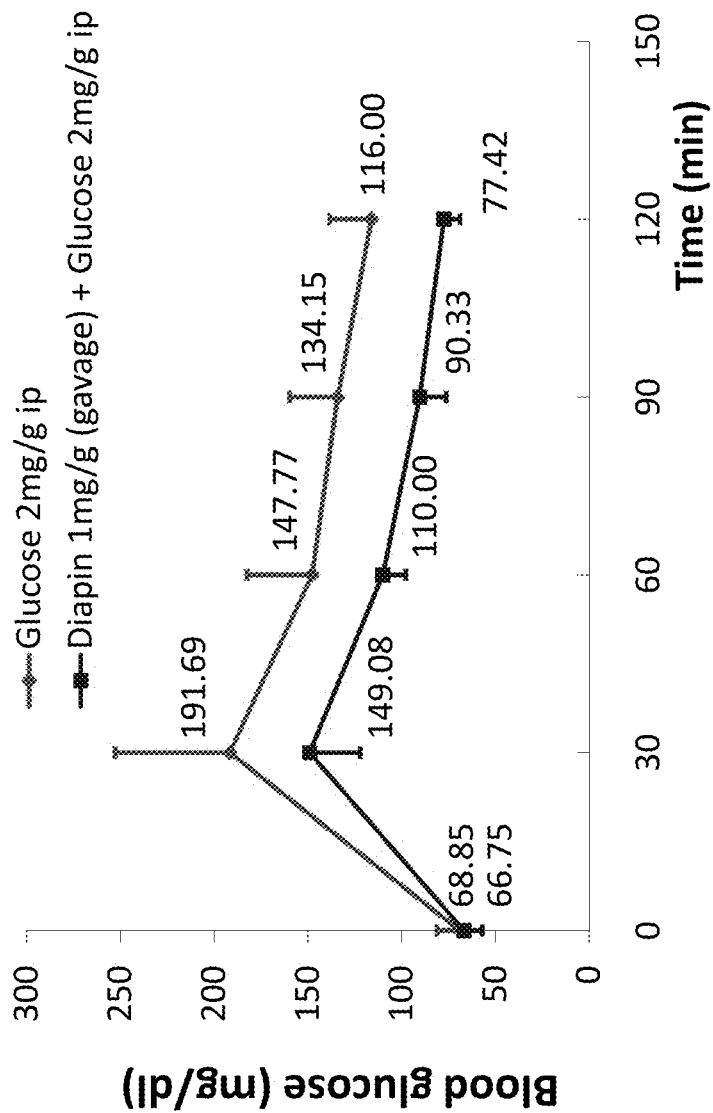
FIG. 10 shows Diapin inhibits the increase in blood glucose after the ip injection of glucose into C57BL/6J mice.

Diapin, LGL, LGG reduce blood glucose levels in non-diabetic C57BL/6J mice after glucose is loaded intraperitoneally. In comparison, the peptide GGH does not.
Diapin Inhibits the Increase of Blood Glucose after the Ip Injection of Glucose An experiment was performed in adult male C57BL/6J mice purchased from Jackson Lab. Fasted mice were given water (diamond line in FIG. 10, n=10) or Diapin orally (1 mg/g bw, square line in FIG. 10, n=10). Glucose was given by ip injection at 10 minutes after the oral administration of Diapin. Blood glucose was measured at 0, 30, 60, 90, 120 min after giving glucose.

Figure 11:
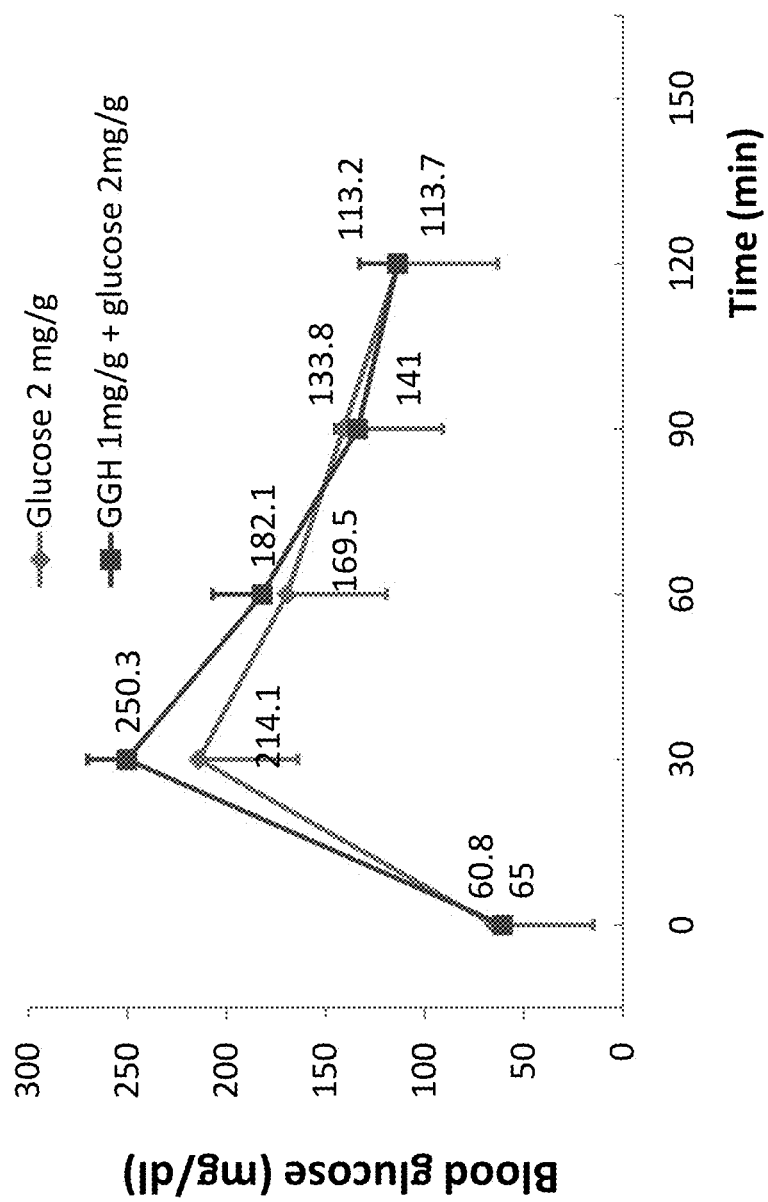
FIG. 11 shows another peptide GGH has no effect on blood glucose after the ip injection of glucose into C57BL/6J mice.

Blood glucose levels at 30, 60, 90 and 120 min in Diapin group were significantly lower than those in the control.
The Peptide GGH has No Significant Effect on Blood Glucose after the Ip Injection of Glucose An experiment was performed in adult male C57BL/6J mice purchased from Jackson Lab. Fasted mice were given water (diamond line in FIG. 11, n=10) or GGH (1 mg/g bw, square line in FIG. 11, n=10). Glucose was given by ip injection at 10 minutes after oral administration of GGH. Blood glucose was measured at 0, 30, 60, 90, 120 min after giving glucose.

Figure 12:
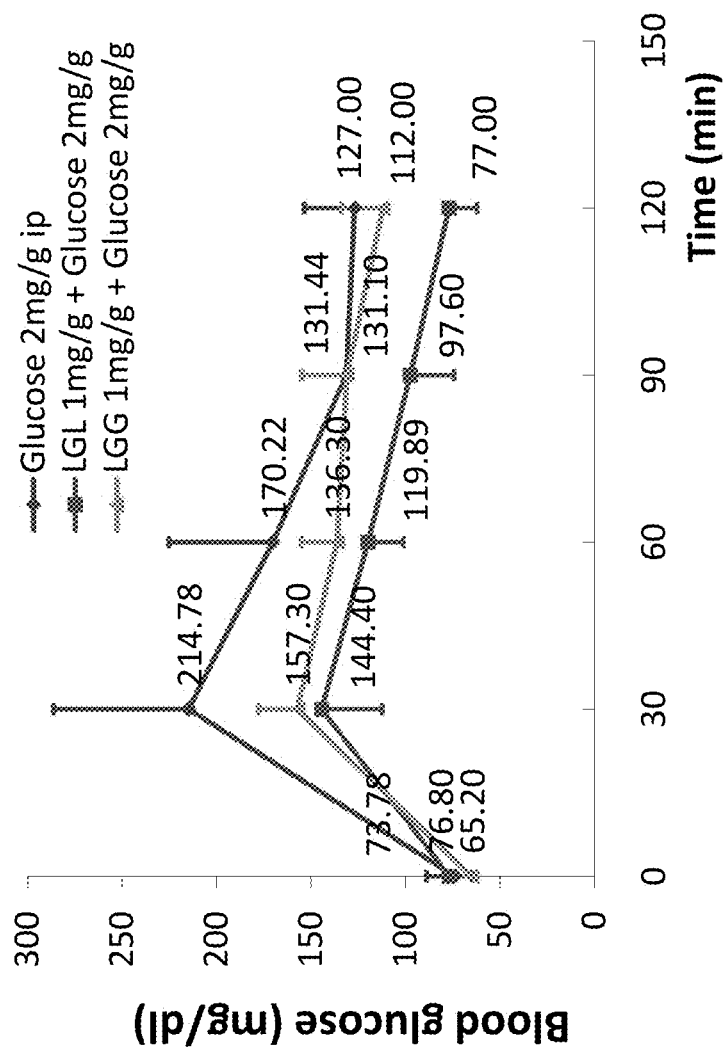
FIG. 12 shows the effect of two other peptides, LGG and LGL, on blood glucose after the ip injection of glucose into C57BL/6J mice.

Blood glucose levels at any time point in the GGH group were not significantly changed compared to the control mice.
The Peptides LGG and LGL Inhibit the Increase in Blood Glucose after the Ip Injection of Glucose An experiment was performed in adult male C57BL/6J mice purchased from Jackson Lab. Fasted mice were given water (diamond line in FIG. 12, n=10) or LGL (1 mg/g bw, square line in FIG. 12, n=10) or LGG (1 mg/g bw, triange line in FIG. 12, n=10). Glucose was given by ip injection 10 minutes after the oral administration of LGG or LGL. Blood glucose was measured at 0, 30, 60, 90, 120 min after giving glucose.

Blood glucose levels at 30, 60, 90 and 120 min in LGL group are significantly lower than those in the control. The peptide LGG reduces the blood glucose levels at 30 and 60 min.

Example 7

Figure 13:
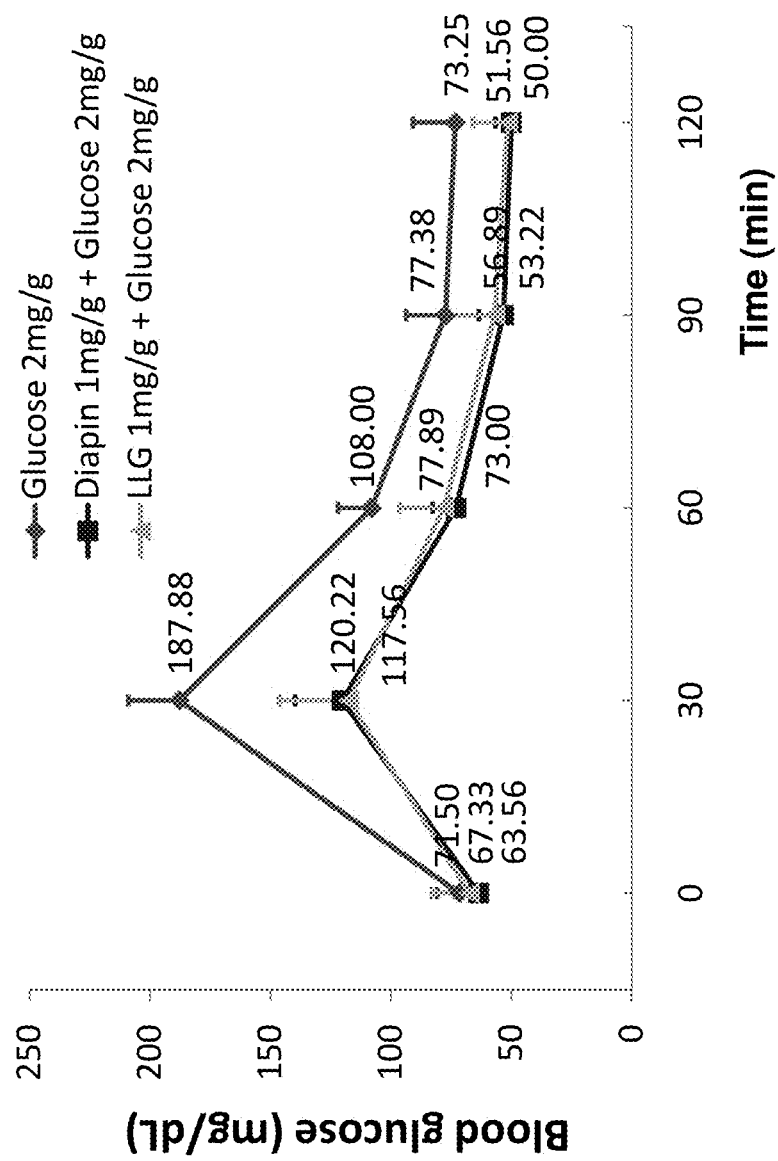
FIG. 13 shows the effect of the peptide LLG on blood glucose after oral load of glucose in C57BL/6J mice.

The peptides LGL, GLG, LLG, and GLL significantly reduce blood glucose levels in non-diabetic C57BL/6J mice loaded with glucose.
Effect of LLG on Blood Glucose after Oral Load of Glucose An experiment was performed in adult male C57BL/6J mice purchased from Jackson Lab. In the control group (diamond line in FIG. 13, n=10), glucose was orally administered at dose of 2 mg/g bw. In the Diapin and LLG group (square line or triangle line, n=9), glucose and Diapin or glucose and LLG were orally administered at dose of 2 mg/g bw and 1 mg/g bw, respectively. Blood glucose was measured at 0, 30, 60, 90 and 120 min after gavaging glucose and Diapin.

Figure 14:
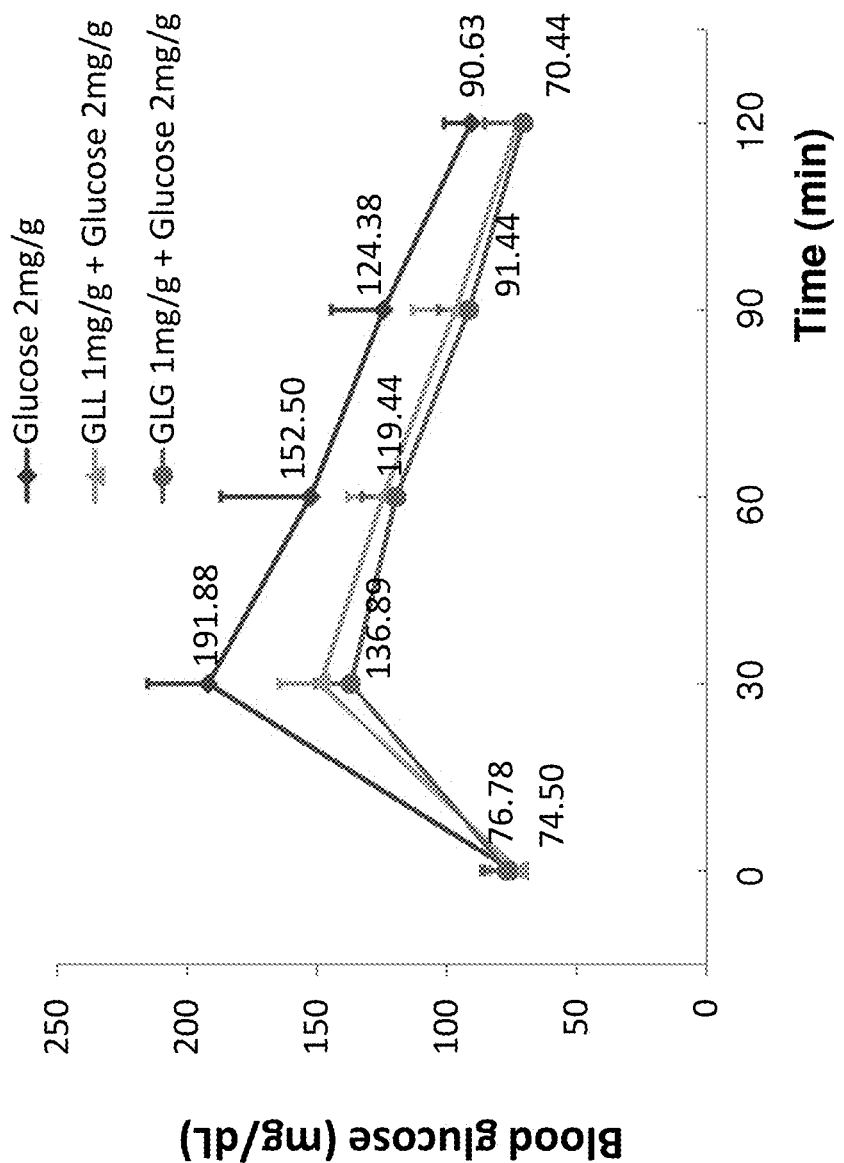
FIG. 14 shows the effect of the peptides GLG and GLL on blood glucose after oral load of glucose in C57BL/6J mice.

LLG showed similar effects to Diapin.
Effect of Peptides GLG and GLL on Blood Glucose after Oral Load of Glucose An experiment was performed in adult male C57BL/6J mice purchased from Jackson Lab. In the control group (diamond line in FIG. 14, n=10), glucose was orally administered at dose of 2 mg/g bw. In the GLG and GLL group (triangle line or circle line in FIG. 14, n=9), glucose and GLG or GLL were orally administered at dose of 2 mg/g bw and 1 mg/g bw, respectively. Blood glucose was measured at 0, 30, 60, 90 and 120 min after gavaging glucose and GLG or GLL.

Peptides GLG and GLL each showed similar effects to Diapin.

Example 8

Figure 15:
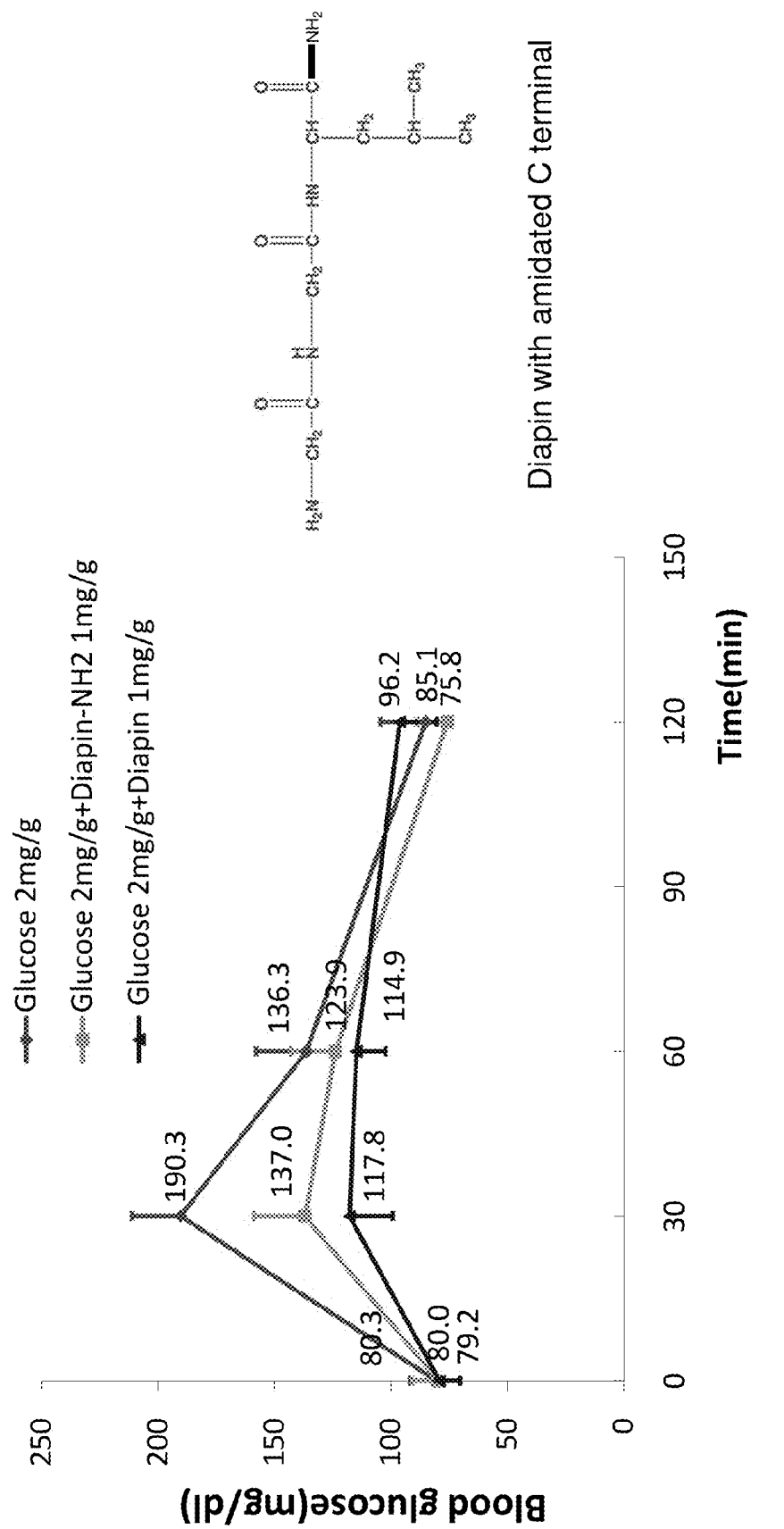
FIG. 15 shows the effect of Diapin and Diapin with an amidated C-terminus on blood glucose after oral administration of glucose in C57BL/6J mice.

Amidation and acetylation do not decrease Diapin glucose reduction. Diapin was amidated by the method described in Bergstrom et al., *J. Biol. Chem.*, 280: 23114-23121 (2005) and/or acetylated by the method described in John et al., *Eur. J. Med. Res.*, 13: 73-78 (2008).
Effect of Amidation on Diapin An experiment was performed in adult male C57BL/6J mice purchased from Jackson Lab. In the control group (diamond line in FIG. 15, n=10), glucose was orally administered at dose of 2 mg/g bw. In the Diapin group (triangle line in FIG. 15, n=9), glucose and Diapin were orally administered at dose of 2 mg/g bw and 1 mg/g bw, respectively. In the amidated Diapin group (square line in FIG. 15, n=9), glucose and amidated Diapin were orally administered at dose of 2 mg/g bw and 1 mg/g bw, respectively. Blood glucose was measured at 0, 0.5, 1, 1.5 and 2 hours after gavaging glucose, Diapin and amidated Diapin.

Figure 16:
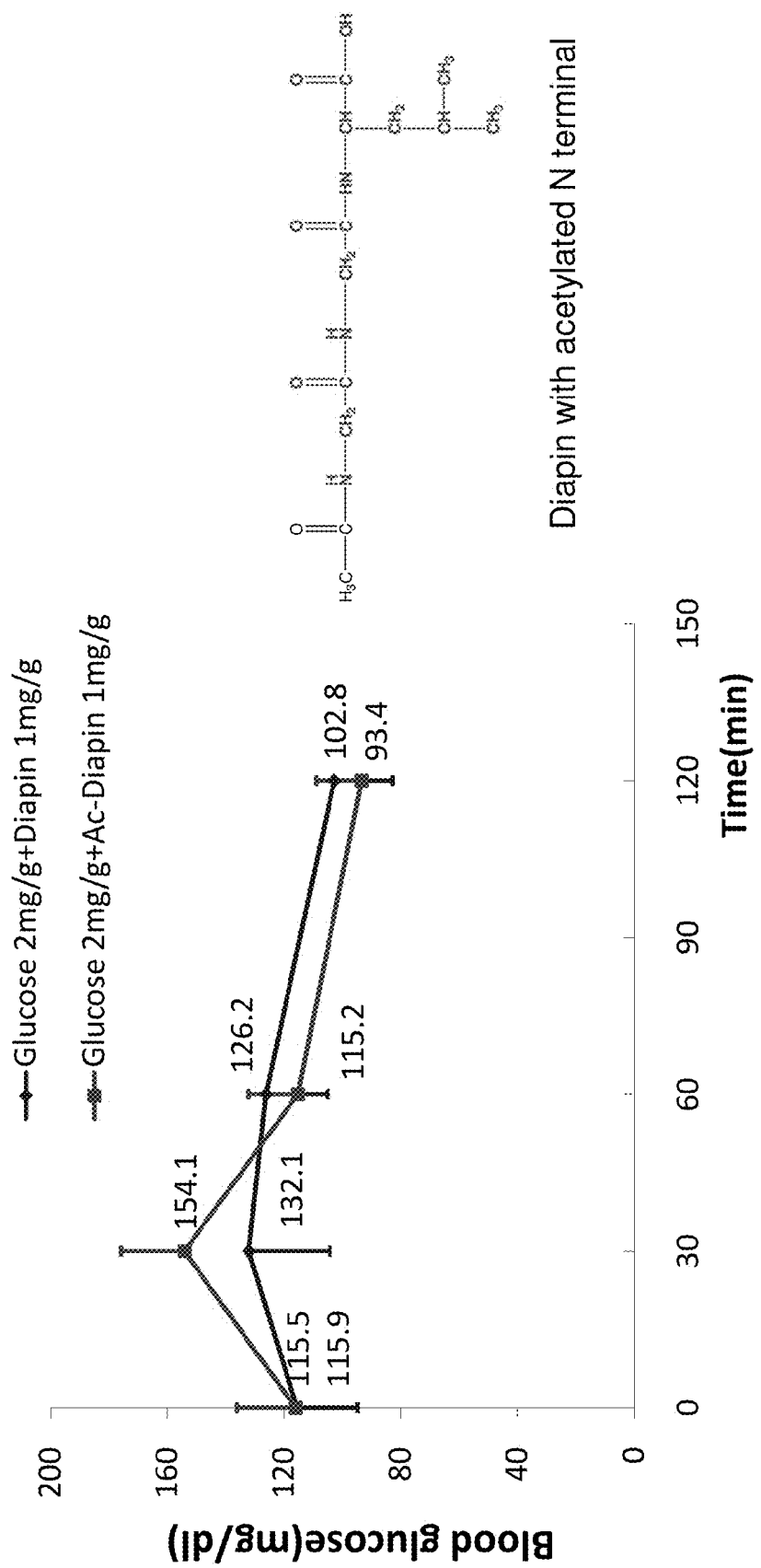
FIG. 16 shows the effect of Diapin and Diapin with an acetylated N-terminus on blood glucose after oral administration of glucose in C57BL/6J mice.

Blood glucose levels at 0, 0.5, 1, 1.5 and 2 hours in the Diapin group and amidated Diapin group were significantly lower than those in the control.
Effect of Acetylation of Diapin An experiment was performed in adult male C57BL/6J mice purchased from Jackson Lab. In the Diapin group (diamond line in FIG. 16, n=10), glucose and Diapin were orally administered at dose of 2 g/kg bw and 1 g/kg bw, respectively. In the acetylated Diapin group (square line in FIG. 16, n=10), glucose and acetylated Diapin were orally administered at dose of 2 g/kg bw and 1 g/kg bw, respectively. Blood glucose was measured at 0, 0.5, 1, 1.5 and 2 hours after gavaging glucose, Diapin, and acetylated Diapin.

Figure 17:
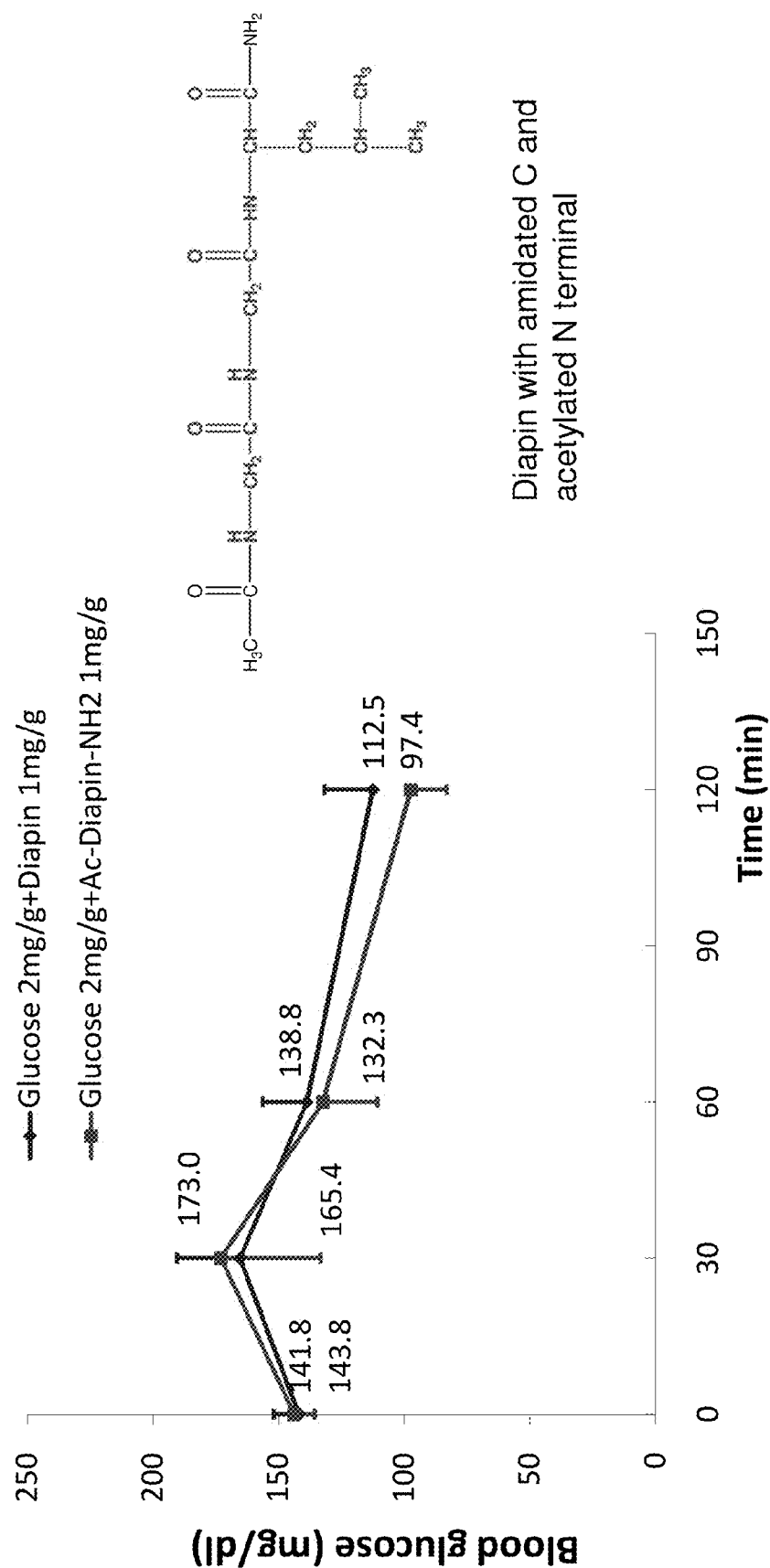
FIG. 17 shows the effect of Diapin with both an amidated C- and acetylated N-terminus on blood glucose after oral administration of glucose in C57BL/6J mice.

Blood glucose levels at 0, 0.5, 1, 1.5 and 2 hours in the Diapin group were not significantly different from those in the acetylated Diapin group.
Effect of Dual Modification on Diapin An experiment was performed in adult male C57BL/6J mice purchased from Jackson Lab. In the Diapin group (triangle line in FIG. 17, n=9), glucose and Diapin were orally administered at dose of 2 g/kg bw and 1 g/kg bw, respectively. In the amidated/acetylated Diapin group (square line, n=9), glucose and amidated/acetylated Diapin were orally administered at dose of 2 g/kg bw and 1 g/kg bw, respectively. Blood glucose was measured at 0, 0.5, 1, 1.5 and 2 hours after gavaging glucose, Diapin and amidated/acetylated Diapin.

Blood glucose levels at 0, 0.5, 1, 1.5 and 2 hours in the Diapin group were not significantly different from those in the amidated/acetylated Diapin group.

Example 9

Figure 18:
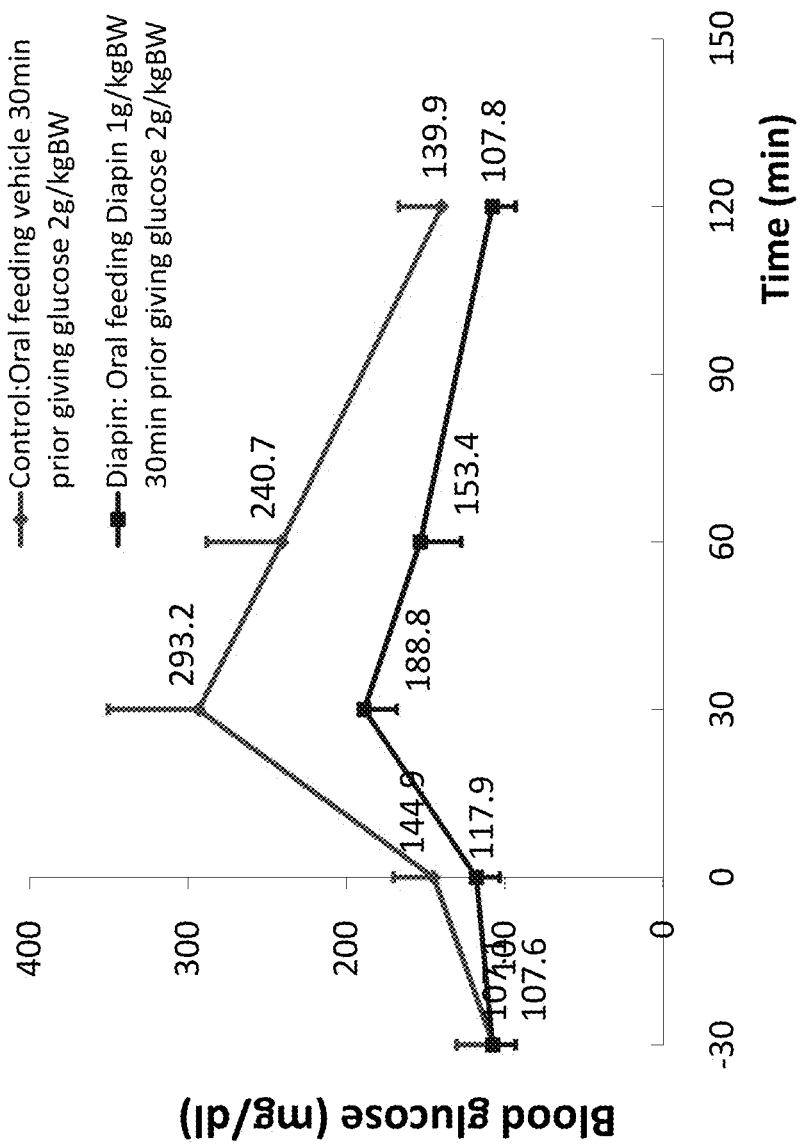
FIG. 18 shows the effect of Diapin given at 30 min prior to oral glucose administration on blood glucose in C57BL/6J mice.

Diapin reduces blood glucose levels when orally administered prior to glucose administration.
Effect of Diapin Given at 30 Min Prior to Oral Glucose Administration An experiment was performed in adult male C57BL/6J mice purchased from Jackson Lab. Fasted mice were given water (diamond line in FIG. 18, n=10) or Diapin (1 mg/g bw, square line in FIG. 18, n=10), then oral gavage glucose 2 g/kg bw after 30 min. Blood glucose was measured at 0, 30, 60 and 120 min after giving glucose.

Figure 19:
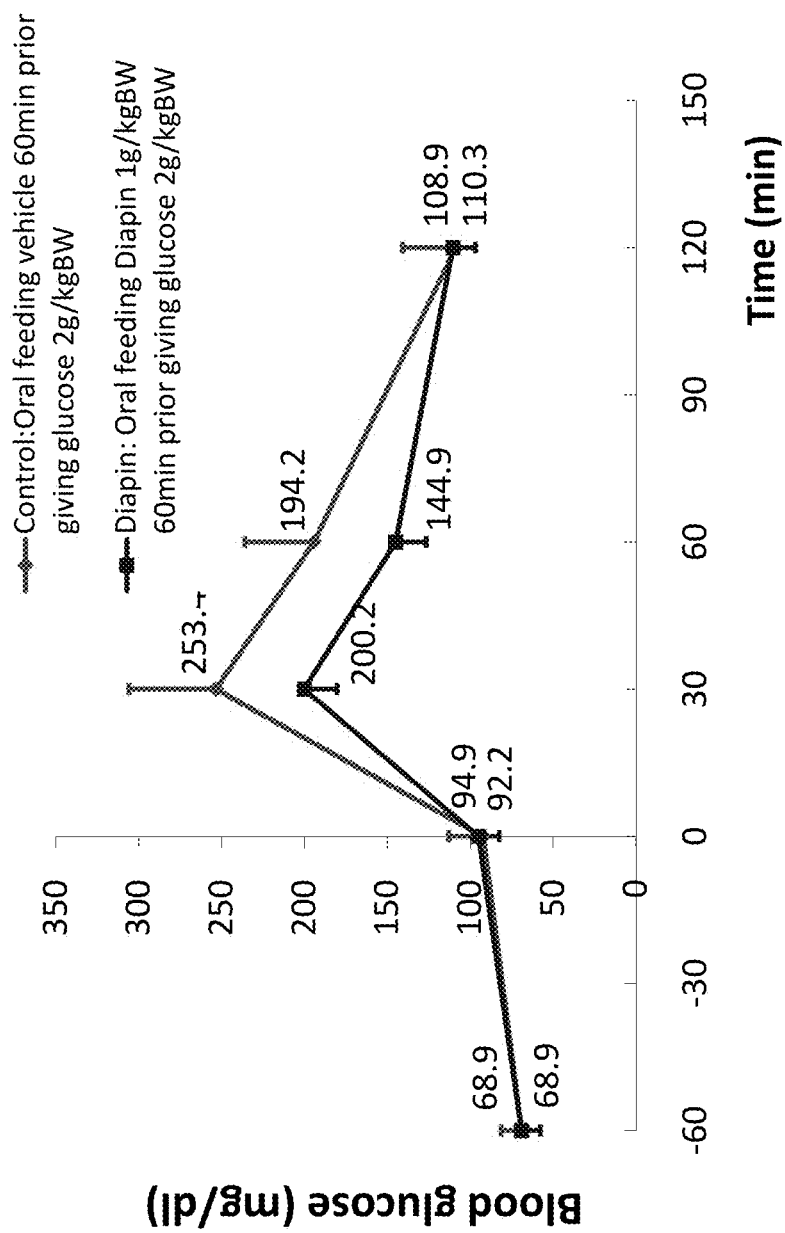
FIG. 19 shows the effect of Diapin given at 1 hour prior to oral glucose administration on blood glucose in C57BL/6J mice.

Blood glucose levels at 30, 60 and 120 min in the Diapin group were significantly lower than those in control group.
Effect of Diapin Given at 1 Hour Prior to Oral Glucose Administration An experiment was performed in adult male C57BL/6J mice purchased from Jackson Lab. Fasted mice were given water (diamond line in FIG. 19, n=10) or Diapin (1 mg/g bw, square line in FIG. 19, n=10), then oral gavage glucose 2 g/kg bw after 1 hour. Blood glucose was measured at 0, 30, 60 and 120 min after giving glucose.

Blood glucose levels at 30, 60 min in the Diapin group were significantly lower than those in control group.

Example 10

Figure 20:
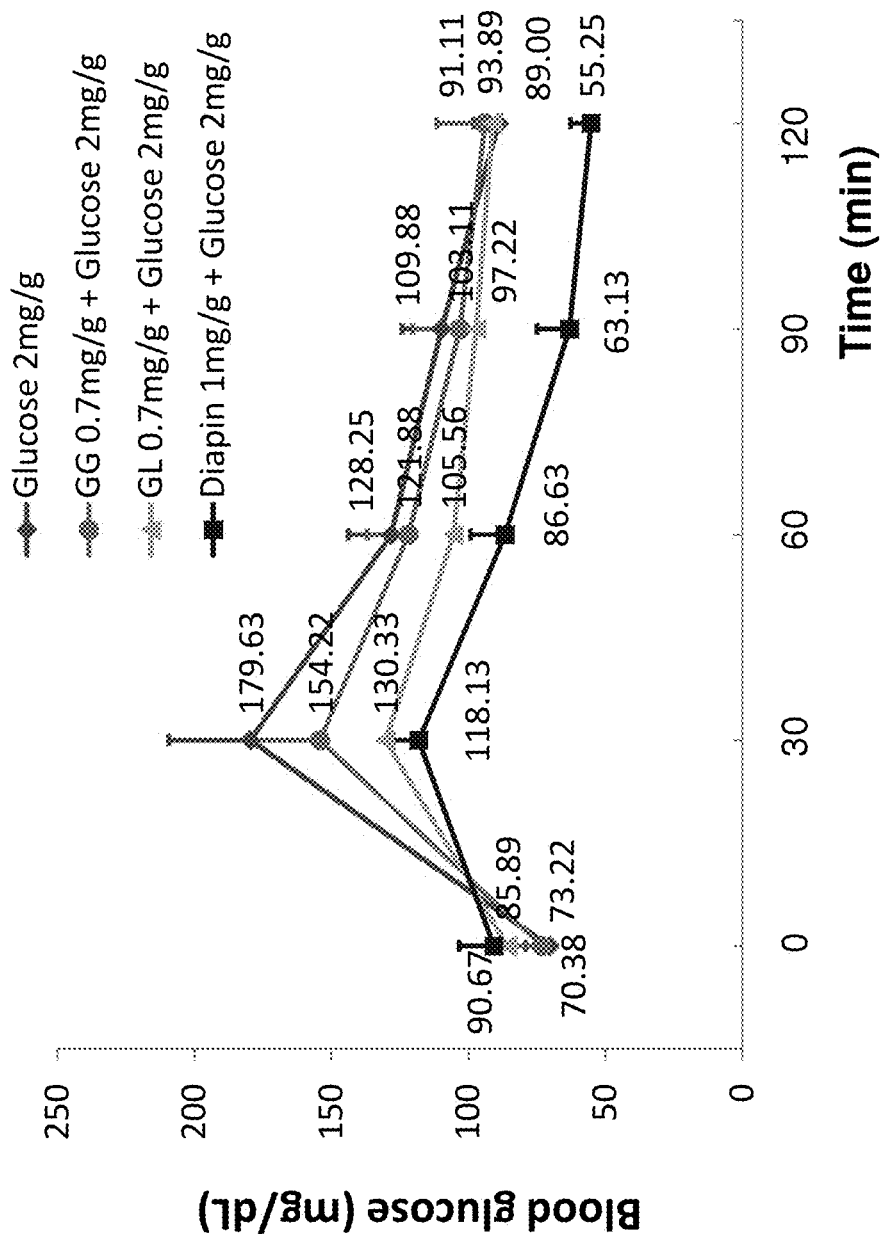
FIG. 20 shows the effect of Diapin and dipeptides on blood glucose level in C57BL/6J mice after oral glucose administration.

Dipeptide GG does not significantly reduce blood glucose levels in C57BL/6J mice after oral glucose administration
Effect of Diapin and Dipeptides GG and GL on Blood Glucose Level after Oral Glucose Administration An experiment was performed in adult male C57BL/6J mice purchased from Jackson Lab. Fasted mice were given glucose 200 mg/kg bw (diamond line in FIG. 20, n=10) or glucose 200 mg/kg bw plus Diapin (square line in FIG. 20, 1 mg/g bw, n=10), GG (circle line in FIG. 20, 0.67 mg/g bw, n=10) or GL (triangle line in FIG. 20, 0.67 mg/g bw, n=10). Blood glucose was measured at 30, 60, 90 and 120 min after giving glucose. Diapin served as a positive control in the experiment.

Figure 21:
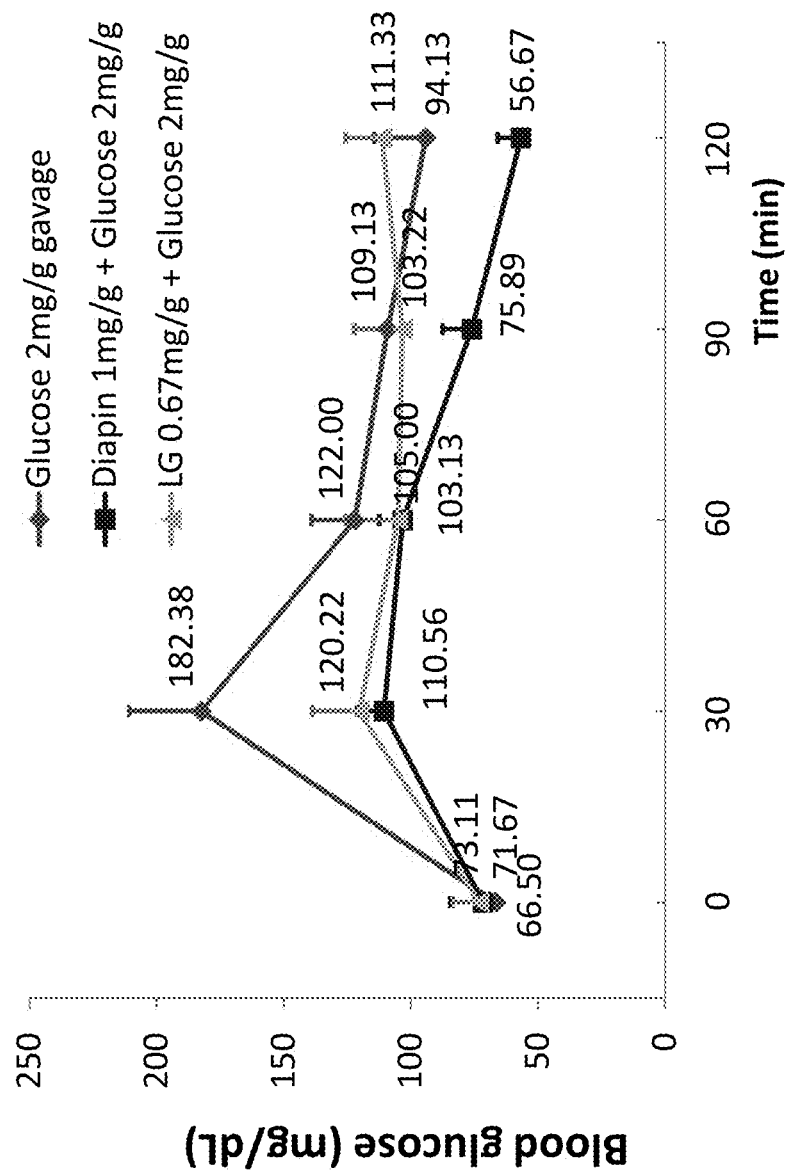
FIG. 21 shows the effect of Diapin and dipeptides on blood glucose level in C57BL/6J mice after oral glucose administration.

Diapin significantly reduced blood glucose levels at 30, 60, 90 and 120 min. Peptide GL reduced the blood glucose level at 30 min while peptide GG did not significantly reduce blood glucose levels in comparison to Diapin.
Effect of Diapin and Dipeptide LG on Blood Glucose Level after Oral Glucose Administration An experiment was performed in adult male C57BL/6J mice purchased from Jackson Lab. Fasted mice were given glucose 200 mg/kg bw (triangle line in FIG. 21, n=10), glucose 200 mg/kg bw plus Diapin (square line in FIG. 21, 1 mg/g bw, n=10), or LG (triangle line in FIG. 21, 0.67 mg/g bw, n=10). Blood glucose was measured at 30, 60, 90 and 120 min after giving glucose. Diapin served as a positive control in the experiments.

The dipeptide LG showed a more transient affect than did Diapin in reducing blood glucose levels. Diapin reduced blood glucose levels at all measured time points, whereas the dipeptide LG reduced blood glucose levels only at 30 and 60 min.

Example 11

Diapin lowers blood glucose level in ob/ob mice [Liu et al., Diabetes, 52(6):1409-16 (2003)] after oral glucose administration.

An experiment was performed in adult male B6.V-Lepob/J mice purchased from Jackson Lab. The fasted mice were given glucose 2 mg/g (n=10) or glucose 2 mg/g bw plus Diapin (1 mg/g bw, n=10) by gavaging. Blood glucose levels were measured at 30, 60, 90 and 120 min after giving glucose and Diapin.

Figure 22:
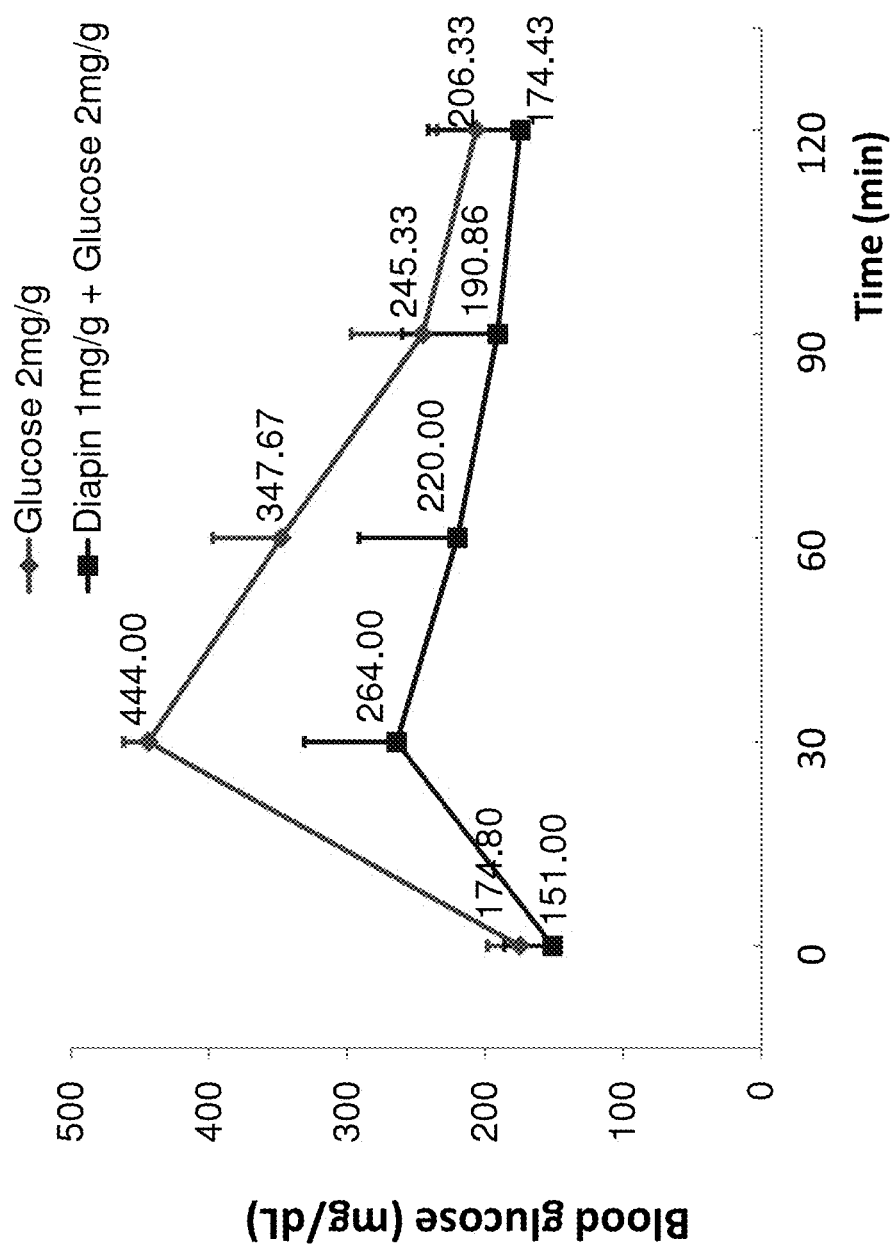
FIG. 22 shows the effect of Diapin in ob/ob mice after oral glucose administration.

As shown in FIG. 22, Diapin inhibits the increase of blood glucose after oral load of glucose in ob/ob mice.

Example 12

Diapin also lowers blood glucose level in db/db mice [Chen et al., *Cell*, (3):491-495 (1996) and Hummel et al., *Science*, 153 (740):1127-1128 (1966)] after oral glucose administration.

The experiment was performed in adult male BKS.Cg-m+/+Leprdb/J mice purchased from Jackson Lab. The fasted mice were given glucose 2 mg/g bw (n=10) or glucose 2 mg/g bw plus Diapin (1 mg/g bw, n=10) by gavaging. Blood glucose levels were measured at 30, 60, 90 and 120 min after giving glucose and Diapin.

Figure 23:
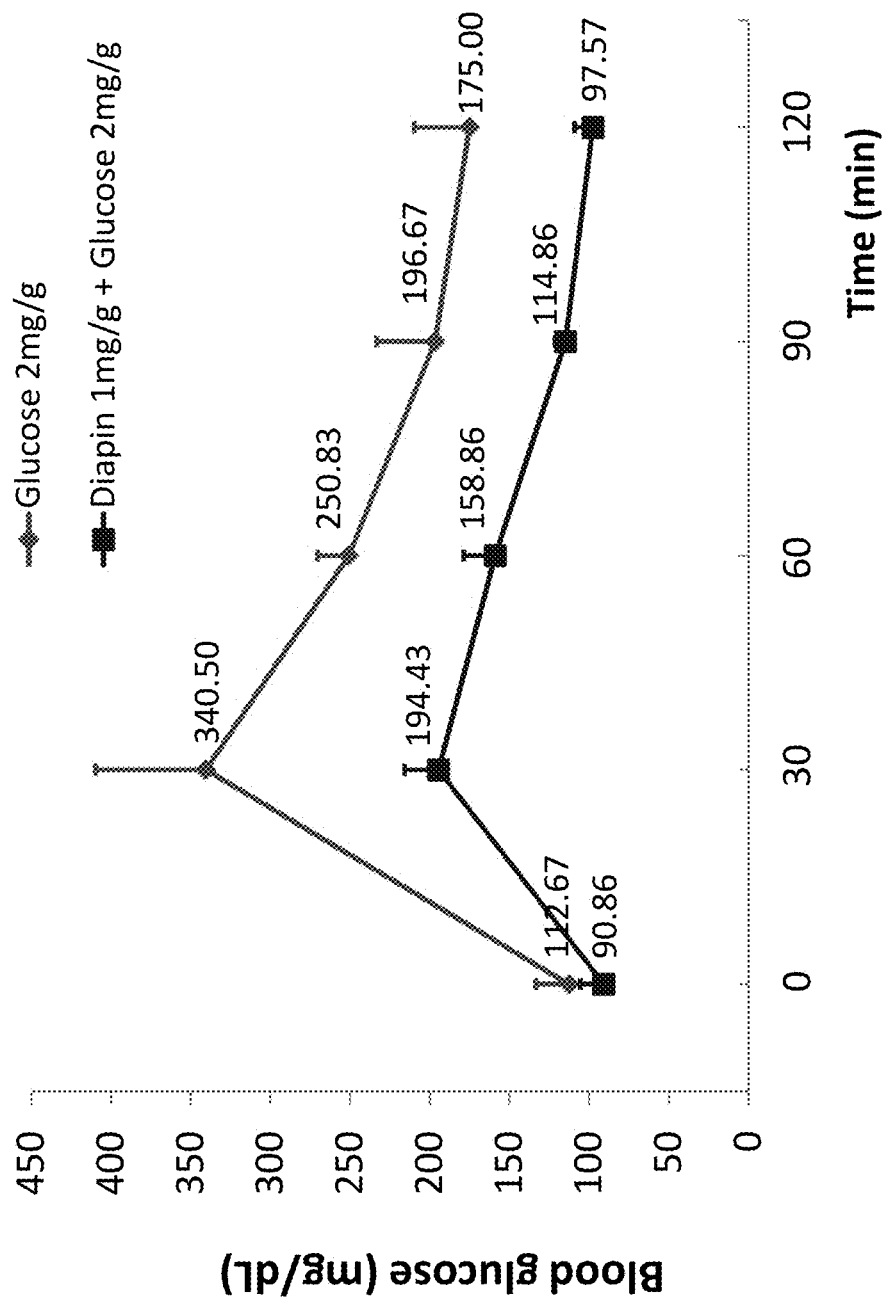
FIG. 23 shows the effect of Diapin on blood glucose level in db/db mice after oral glucose administration.

As shown in FIG. 23, Diapin inhibits the increase of blood glucose after oral load of glucose in db/db mice.

Example 13

Diapin lowers blood glucose level in high fat diet-induced diabetic mice [Tomas et al., *Diabetes Obes. Metab.*, 13(1): 26-33 (2011) and Dezaki et al., *Diabetes*, 55 (12):3486-93 (2006)] after oral glucose administration.

Wild type male C57BL/6J mice purchased from Jackson Lab were fed with high fat diet [rodent diet with 60% of calories from fat (Research Diets Inc. Cat#: D12492)] for eight weeks to induce obesity with insulin resistance mouse model. Then, the fasted mice were given glucose 2 mg/g bw (n=10) or glucose 2 mg/g bw plus Diapin (1 mg/g bw, n=10) by gavaging. Blood glucose levels were measured at 30, 60, 90 and 120 min after giving glucose and Diapin.

Figure 24:
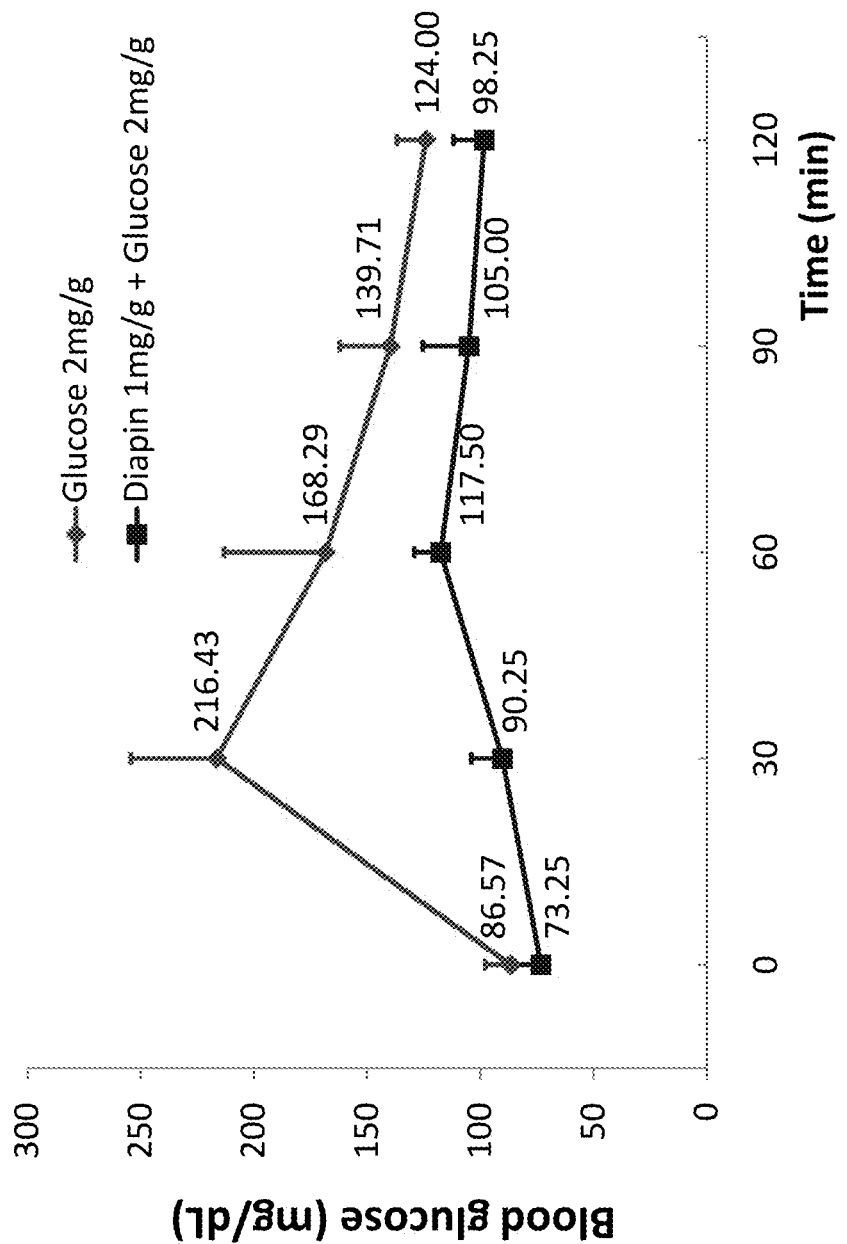
FIG. 24 shows the effect of Diapin on blood glucose level in high fat diet-induced diabetic mice after oral glucose administration.

As shown in FIG. 24, Diapin inhibits the increase of blood glucose after oral load of glucose in high fat diet-induced diabetic mice.

Example 14

Glycine-Glycine-D-Leucine (D-Diapin) has an extended effect on lowering blood glucose level in C57BL/6J mice after oral glucose administration.

An experiment was performed in adult male C57BL/6J mice purchased from Jackson Lab. The fasted mice were given glucose 2 mg/g bw (n=10) or glucose 2 mg/g bw plus D-Diapin (1 mg/g bw, n=10) or Diapin (1 mg/g bw, n=10) by gavaging. Blood glucose levels were measured at 30, 60, 90, 120, and 180 min after giving glucose.

Figure 25:
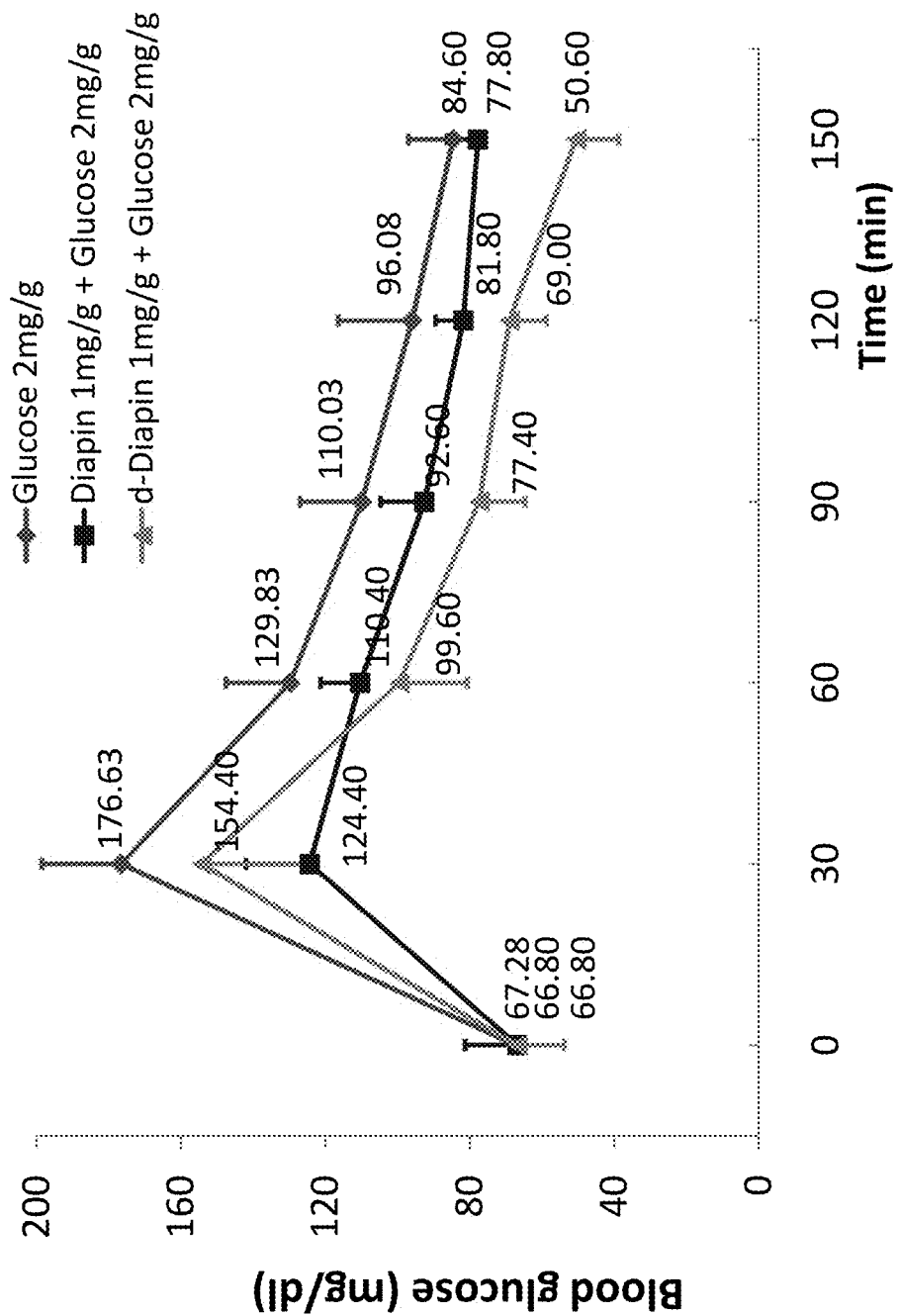
FIG. 25 shows the effect of D-Diapin (composed of D-isomer amino acids) on lowering blood glucose level in C57BL/6J mice after oral glucose administration.

As shown in FIG. 25, D-Diapin is more effective than Diapin in lowering blood glucose levels after oral load of glucose in C57BL/6J mice.

Example 15

Diapin lowers blood glucose level in C57BL/6J mice after oral glucose administration and ip Diapin administration.

Figure 26:
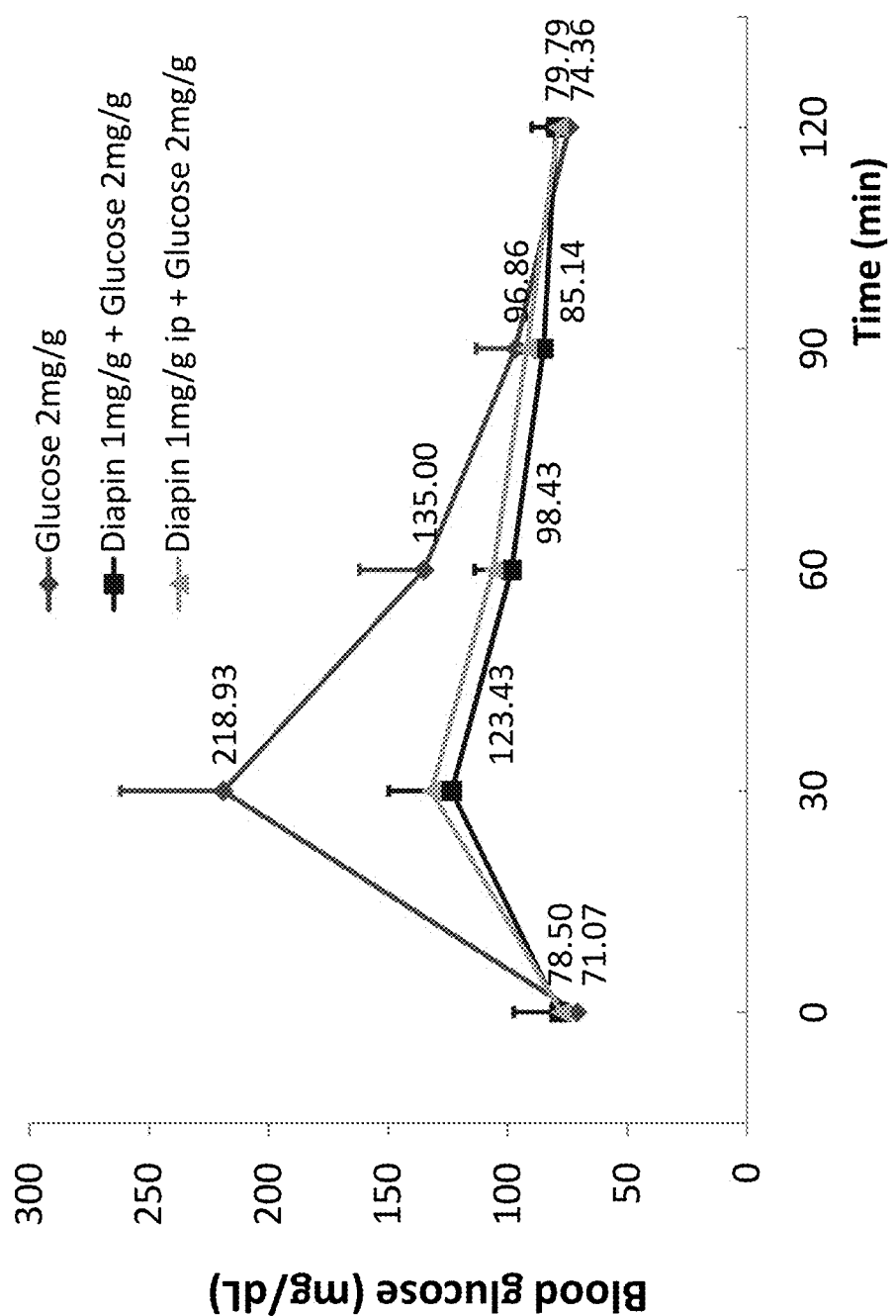
FIG. 26 shows the effect of Diapin on blood glucose level in C57BL/6J mice after oral glucose administration and ip Diapin administration.

The experiment was performed in adult male C57BL/6J mice purchased from Jackson Lab. The fasted mice were given glucose 2 mg/g bw (n=14) or glucose 2 mg/g bw plus Diapin (1 mg/g bw, ip, n=14) or Diapin (1 mg/g bw, n=14) by gavaging. Blood glucose was measured at 30, 60, 90 and 120 min after giving glucose and Diapin. Results are shown in FIG. 26.

Example 16

Modified dipeptides had different effects on blood glucose level in C57BL/6J mice after oral glucose administration. The modified dipeptides tested were an amidated GL dipeptide and the D-isomer of dipeptide LG.

Figure 27:
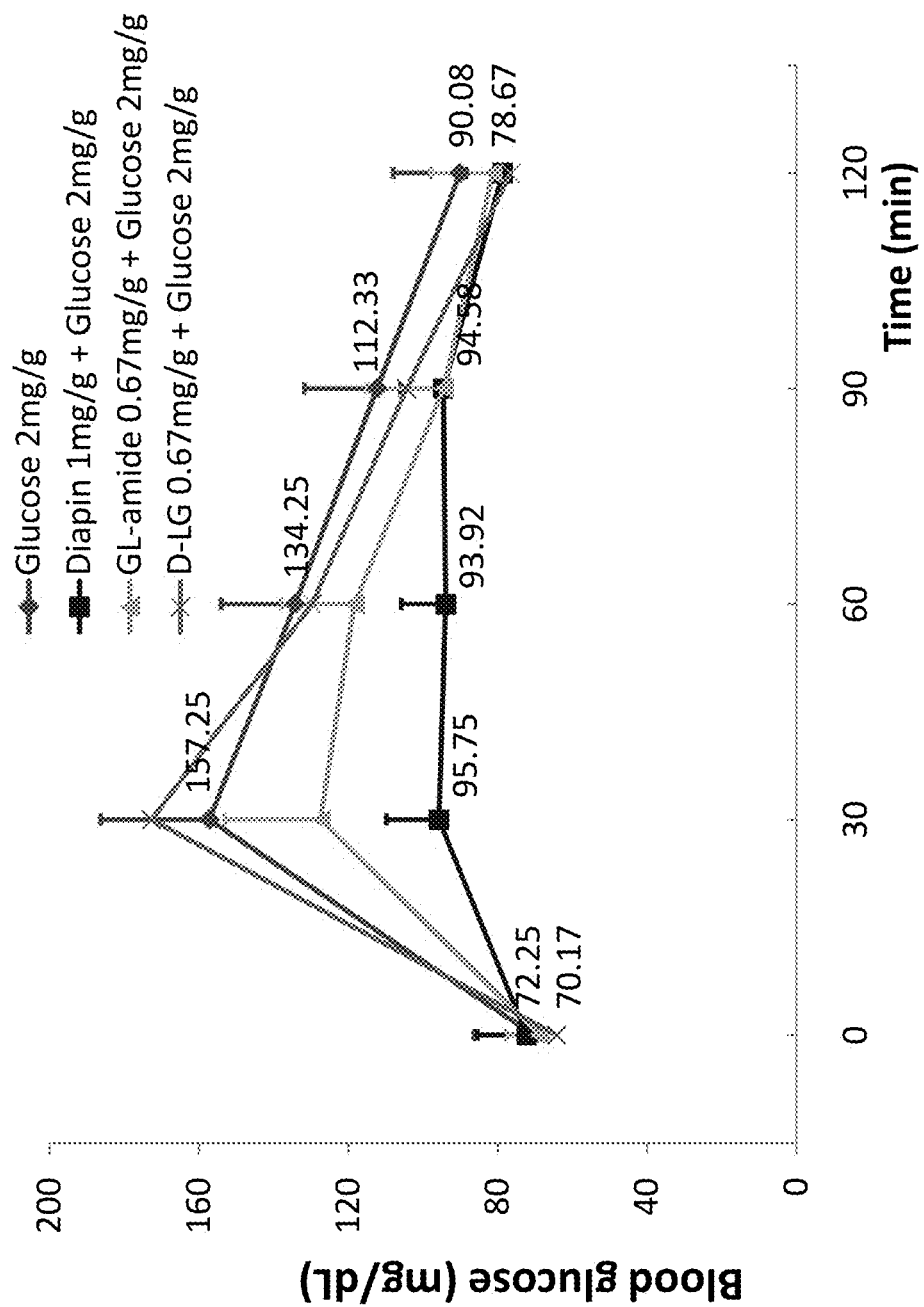
FIG. 27 shows the effect of modified dipeptides on blood glucose level in C57BL/6J mice after oral glucose administration.

An experiment was performed in adult male C57BL/6J mice purchased from Jackson Lab. The fasted mice were given glucose 2 mg/g bw (n=12) or glucose 2 mg/g bw plus Diapin (1 mg/g bw, ip, n=12) or dipeptide (0.67 mg/g bw, n=12) by gavaging. Blood glucose was measured at 30, 60, 90 and 120 min after giving glucose and peptide. Results are shown in FIG. 27.

While the present invention has been described in terms of specific embodiments, it is understood that variations and modifications will occur to those skilled in the art. Accordingly, only such limitations as appear in the claims should be placed on the invention.

All documents cited in this application are hereby incorporated by reference in their entirety for their disclosure described.

We claim:

1. A method for treating a condition comprising administering to a patient an effective amount of a composition, wherein the composition comprises:
   - at least one peptide consisting of the amino acid sequence GGL, GLG, LGL, LLG, LGG, GLL, GGdL, GdLG, GdLL, GLdL, GdLdL, dLLG, LdLG, dLdLG, dLGG, dLGL, LGdL, or dLGdL, or a pharmaceutically acceptable salt of the peptide;
   - at least one peptide consisting of the amino acid sequence GGL, GLG, LGL, LLG, LGG, GLL, GGdL, GdLG, GdLL, GLdL, GdLdL, dLLG, LdLG, dLdLG, dLGG, dLGL, LGdL, or dLGdL, or a pharmaceutically acceptable salt of the peptide, wherein the peptide is acetylated at the N-terminus;
   - at least one peptide consisting of the amino acid sequence GGL, GLG, LGL, LLG, LGG, GLL, GGdL, GdLG, GdLL, GLdL, GdLdL, dLLG, LdLG, dLdLG, dLGG, dLGL, LGdL, or dLGdL, or a pharmaceutically acceptable salt of the peptide, wherein the peptide is amidated at the C-terminus; or
   - at least one peptide consisting of the amino acid sequence GGL, GLG, LGL, LLG, LGG, GLL, GGdL, GdLG, GdLL, GLdL, GdLdL, dLLG, LdLG, dLdLG, dLGG, dLGL, LGdL, or dLGdL, or a pharmaceutically acceptable salt of the peptide, wherein the peptide is acetylated at the N-terminus and amidated at the C-terminus; and
   - wherein the condition is prediabetes, diabetes, obesity, high blood pressure, metabolic syndrome, poor glycemic control, or reduced insulin secretion.

2. The method according to claim 1, wherein the at least one peptide consists of the amino acid sequence GGL, GLG, LGL, LLG, LGG, GLL, or any mixture thereof.

3. The method according to claim 1, wherein the at least one peptide consists of the amino acid sequence GGdL, GdLG, GdLL, GLdL, GdLdL, dLLG, LdLG, dLdLG, dLGG, dLGL, LGdL, dLGdL, or any mixture thereof.

4. The method of claim 1, wherein the composition is administered by an oral, intraperitoneal, ocular, intradermal, intranasal, subcutaneous, intramuscular or intravenous route.

5. The method of claim 4, wherein the composition is administered by an oral route.

6. The method according to claim 2, wherein the condition is prediabetes or diabetes.

7. The method according to claim 3, wherein the condition is prediabetes or diabetes.

8. The method according to claim 2, wherein the condition is obesity, high blood pressure or metabolic syndrome.

9. The method according to claim 3, wherein the condition is obesity, high blood pressure or metabolic syndrome.

10. The method according to claim 2, wherein the at least one peptide consists of the amino acid sequence GGL.

11. The method according to claim 3, wherein the at least one peptide consists of the amino acid sequence GGdL.

12. A method of preventing, reducing, or ameliorating a diabetes-associated complication in a diabetic patient comprising administering to the patient an effective amount of a composition, wherein the composition comprises:
- at least one peptide consisting of the amino acid sequence GGL, GLG, LGL, LLG, LGG or GLL, GGdL, GdLG, GdLL, GLdL, GdLdL, dLLG, LdLG, dLdLG, dLGG, dLGL, LGdL or dLGdL, or a pharmaceutically acceptable salt of the peptide;
- at least one peptide consisting of the amino acid sequence GGL, GLG, LGL, LLG, LGG, GLL, GGdL, GdLG, GdLL, GLdL, GdLdL, dLLG, LdLG, dLdLG, dLGG, dLGL, LGdL, or dLGdL, or a pharmaceutically acceptable salt of the peptide, wherein the peptide is acetylated at the N-terminus;
- at least one peptide consisting of the amino acid sequence GGL, GLG, LGL, LLG, LGG, GLL, GGdL, GdLG, GdLL, GLdL, GdLdL, dLLG, LdLG, dLdLG, dLGG, dLGL, LGdL, or dLGdL, or a pharmaceutically acceptable salt of the peptide, wherein the peptide is amidated at the C-terminus; or
- at least one peptide consisting of the amino acid sequence GGL, GLG, LGL, LLG, LGG, GLL, GGdL, GdLG, GdLL, GLdL, GdLdL, dLLG, LdLG, dLdLG, dLGG, dLGL, LGdL, or dLGdL, or a pharmaceutically acceptable salt of the peptide, wherein the peptide is acetylated at the N-terminus and amidated at the C-terminus.

13. The method according to claim 12, wherein the at least one peptide consists of the amino acids GGL, GLG, LGL, LLG, LGG or GLL, or any mixture thereof.

14. The method according to claim 12, wherein the at least one peptide consists of the amino acids GGdL, GdLG, GdLL, GLdL, GdLdL, dLLG, LdLG, dLdLG, dLGG, dLGL, LGdL or dLGdL, or any mixture thereof.

15. The method of claim 12, wherein the composition is administered by an oral, intraperitoneal, ocular, intradermal, intranasal, subcutaneous, intramuscular or intravenous route.

16. The method of claim 15, wherein the composition is administered by an oral route.

17. The method according to claim 13, wherein the diabetes-associated complication is a cardiovascular disease, chronic kidney disease, kidney failure, bladder problems, erectile dysfunction, gastroporesis, an eye disease, a diabetic neuropathy, foot or skin ulcers, or lower extremity amputation.

18. The method according to claim 14, wherein the diabetes-associated complication is a cardiovascular disease, chronic kidney disease, kidney failure, bladder problems, erectile dysfunction, gastroporesis, an eye disease, a diabetic neuropathy, foot or skin ulcers, or lower extremity amputation.

19. The method according to claim 13, wherein the at least one peptide consists of the amino acid sequence GGL.

20. The method according to claim 14, wherein the at least one peptide consists of the amino acid sequence GGdL.

* * * * *